(12) United States Patent
Ohgi et al.

(10) Patent No.: US 9,404,108 B2
(45) Date of Patent: Aug. 2, 2016

(54) MICRO-RMA INHIBITOR

(71) Applicant: BONAC CORPORATION, Kurume-shi, Fukuoka (JP)

(72) Inventors: Tadaaki Ohgi, Kurume (JP); Hisao Shirohzu, Kurume (JP); Hiroshi Suzuki, Itami (JP); Tomohiro Hamasaki, Kurume (JP); Takayuki Mizutani, Kurume (JP)

(73) Assignee: Bonac Corporation, Kurume (JP)

( * ) Notice: Subject to any disclaimer, the term of this patent is extended or adjusted under 35 U.S.C. 154(b) by 0 days.

(21) Appl. No.: 14/383,043

(22) PCT Filed: Mar. 4, 2013

(86) PCT No.: PCT/JP2013/055868
§ 371 (c)(1),
(2) Date: Sep. 4, 2014

(87) PCT Pub. No.: WO2013/133221
PCT Pub. Date: Sep. 12, 2013

(65) Prior Publication Data
US 2015/0073124 A1    Mar. 12, 2015

(30) Foreign Application Priority Data

Mar. 4, 2012    (JP) .................................. 2012-047466

(51) Int. Cl.
| | | |
|---|---|---|
| *C12N 15/113* | (2010.01) | |
| *A61K 31/7105* | (2006.01) | |
| *C12N 15/11* | (2006.01) | |
| *C07F 9/22* | (2006.01) | |
| *A61K 47/48* | (2006.01) | |

(52) U.S. Cl.
CPC .......... *C12N 15/113* (2013.01); *A61K 31/7105* (2013.01); *A61K 47/48092* (2013.01); *C07F 9/222* (2013.01); *C12N 15/111* (2013.01); *C12N 2310/113* (2013.01); *C12N 2310/14* (2013.01); *C12N 2310/318* (2013.01); *C12N 2310/351* (2013.01); *C12N 2310/3513* (2013.01); *C12N 2310/3519* (2013.01); *C12N 2310/51* (2013.01)

(58) Field of Classification Search
USPC .................. 435/6.1, 91.1, 91.31, 375; 514/44; 536/23.1, 24.5; 530/300, 331; 564/12
See application file for complete search history.

(56) References Cited

U.S. PATENT DOCUMENTS

| | | | |
|---|---|---|---|
| 2010/0279408 A1 | 11/2010 | Zhao | |
| 2011/0245481 A1 | 10/2011 | Iba et al. | |
| 2012/0035246 A1 | 2/2012 | Ohgi et al. | |
| 2012/0041184 A1* | 2/2012 | Beigelman et al. | 536/24.5 |
| 2013/0123462 A1* | 5/2013 | Dimarchi et al. | 530/308 |
| 2014/0329886 A1 | 11/2014 | Ohgi et al. | |

FOREIGN PATENT DOCUMENTS

| | | |
|---|---|---|
| JP | 2005-517452 A | 6/2005 |
| JP | 2010-510810 A | 4/2010 |
| WO | WO 03/070969 A2 | 8/2003 |
| WO | WO 2010/047216    * | 4/2010 |
| WO | WO 2010/047216 A1 | 4/2010 |
| WO | WO 2011/117353 A1 | 9/2011 |
| WO | WO 2011/130371 A1 | 10/2011 |
| WO | WO 2012/017919 A1 | 2/2012 |
| WO | WO 2013/103146 A1 | 5/2015 |

OTHER PUBLICATIONS

Ebert et al, Nature Methods, vol. 4, No. 9, pp. 721-726 (2007).*
Haraguchi et al, Nucleic Acids Res., vol. 37, No. 6, e43 (2009).*
DePaula et al, RNA, vol. 13, pp. 431-456 (2007).*
Ebert et al., *Nature Methods*, 4(9): 721-726 (2007).
Haraguchi et al., *Nucleic Acids Res.*, 37(6): e43 (2009).
Haraguchi et al., *Seitai no Kagaku*, 61(4): 326-331 (2010).
Obad et al., *Nature Genetics*, 43(4): 371-378 (2011).
Vermeulen et al., *RNA*, 13: 723-730 (2007).
Japanese Patent Office, International Search Report in International Patent Application No. PCT/JP2013/055868 (Mar. 26, 2013).
Japanese Patent Office, Written Opinion in International Patent Application No. PCT/JP2013/055868 (Mar. 26, 2013).
European Patent Office, Supplementary European Search Report in European Patent Application No. 13757229 (Jan. 5, 2016).
Odake et al., "Inhibition of Urease Activity by Dipeptidyl Hydroxamic Acids," *Chem. Pharm. Bull.*, 40(10): 2764-2768 (1992).
U.S. National Library of Medicine, National Center for Biotechnology Information, PubChem Open Chemistry Database, Compound Summary for CID 24643620 [Zinc22697184] (Feb. 29, 2008).
Fabani et al., *RNA*, 14(2): 336-346 (2008).
Stenvang et al., *Silence*, 3(1): 1-17 (2012).
European Patent Office, Supplementary Partial European Search Report in European Patent Application No. 13757229 (Oct. 2, 2015).

* cited by examiner

*Primary Examiner* — Jane Zara
(74) *Attorney, Agent, or Firm* — Leydig, Voit & Mayer, Ltd.

(57) ABSTRACT

The invention provides a microRNA inhibitor that has two or more sequences complementary to the sequence of microRNA to be the target of inhibition, which two or more complementary sequences are linked via one or more linker residues.

2 Claims, 10 Drawing Sheets

5'- X=cacaaaccatgcctgctgcta=X=cacaaaccatgcctgctgcta=X=cacaaaccatgcctgctgcta=X -3'

X is glycine residue (a)

(b)

(c)

SEQUENCE LISTING

```
<160> NUMBER OF SEQ ID NOS: 19

<210> SEQ ID NO 1
<211> LENGTH: 21
<212> TYPE: DNA
<213> ORGANISM: Artificial Sequence
<220> FEATURE:
<223> OTHER INFORMATION: Synthetic DNA

<400> SEQUENCE: 1
cacaaaccat gcctgctgct a                                          21

<210> SEQ ID NO 2
<211> LENGTH: 64
<212> TYPE: DNA
<213> ORGANISM: Artificial Sequence
<220> FEATURE:
<223> OTHER INFORMATION: Synthetic DNA

<400> SEQUENCE: 2
cgccaatatt cgatgctgct acgccaatat tcgatgctgc tacgccaata ttcgatgctg    60
ctat                                                               64

<210> SEQ ID NO 3
<211> LENGTH: 22
<212> TYPE: DNA
<213> ORGANISM: Artificial Sequence
<220> FEATURE:
<223> OTHER INFORMATION: Synthetic DNA

<400> SEQUENCE: 3
cgccaatatt cgatgctgct at                                          22

<210> SEQ ID NO 4
<211> LENGTH: 67
<212> TYPE: DNA
```

<213> ORGANISM: Artificial Sequence
<220> FEATURE:
<223> OTHER INFORMATION: Synthetic DNA

<400> SEQUENCE: 4

```
cgccaatatt tacgtgctgc tacgccaata tttacgtgct gctacgccaa tatttacgtg    60
ctgctat                                                              67
```

<210> SEQ ID NO 5
<211> LENGTH: 23
<212> TYPE: DNA
<213> ORGANISM: Artificial Sequence
<220> FEATURE:
<223> OTHER INFORMATION: Synthetic DNA

<400> SEQUENCE: 5

```
cgccaatatt tacgtgctgc tat                                            23
```

<210> SEQ ID NO 6
<211> LENGTH: 64
<212> TYPE: DNA
<213> ORGANISM: Artificial Sequence
<220> FEATURE:
<223> OTHER INFORMATION: Synthetic DNA

<400> SEQUENCE: 6

```
cgccaatatt cgatgctgct acgccaatat tcgatgctgc tacgccaata ttcgatgctg    60
ctat                                                                 64
```

<210> SEQ ID NO 7
<211> LENGTH: 22
<212> TYPE: DNA
<213> ORGANISM: Artificial Sequence
<220> FEATURE:
<223> OTHER INFORMATION: Synthetic DNA

<400> SEQUENCE: 7

```
cgccaatatt cgatgctgct at                                             22
```

<210> SEQ ID NO 8
<211> LENGTH: 64
<212> TYPE: DNA
<213> ORGANISM: Artificial Sequence
<220> FEATURE:
<223> OTHER INFORMATION: Synthetic DNA

<400> SEQUENCE: 8

```
cgccaatatt ccattataag acgccaatat tccattataa gacgccaata ttccattata    60
agat                                                                 64
```

<210> SEQ ID NO 9
<211> LENGTH: 67
<212> TYPE: DNA
<213> ORGANISM: Artificial Sequence
<220> FEATURE:
<223> OTHER INFORMATION: Synthetic DNA

<400> SEQUENCE: 9

```
cgccaatatt tacgtaatta cacgccaata tttacgtaat tacacgccaa tatttacgta    60
attacat                                                              67
```

<210> SEQ ID NO 10
<211> LENGTH: 64

```
<212> TYPE: DNA
<213> ORGANISM: Artificial Sequence
<220> FEATURE:
<223> OTHER INFORMATION: Synthetic DNA

<400> SEQUENCE: 10
cgccaatatt ccattataag acgccaatat tccattataa gacgccaata ttccattata    60
agat                                                                 64

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA

<400> SEQUENCE: 11
gccaatattt acgtgctgct                                                20

<210> SEQ ID NO 12
<211> LENGTH: 20
<212> TYPE: DNA
<213> ORGANISM: Artificial Sequence
<220> FEATURE:
<223> OTHER INFORMATION: Synthetic DNA

<400> SEQUENCE: 12
agagctccct tcaatccaaa                                                20

<210> SEQ ID NO 13
<211> LENGTH: 64
<212> TYPE: RNA
<213> ORGANISM: Artificial Sequence
<220> FEATURE:
<223> OTHER INFORMATION: Synthetic RNA

<400> SEQUENCE: 13 cgccauauu cgaugcugcu acgccaauau ucgaugcugc uacgccaaua uucgaugcug     60
cuau                                                                 64

<210> SEQ ID NO 14
<211> LENGTH: 64
<212> TYPE: RNA
<213> ORGANISM: Artificial Sequence
<220> FEATURE:
<223> OTHER INFORMATION: Synthetic RNA

<400> SEQUENCE: 14
cgccaauauu ccauuauaag acgccaauau uccauuauaa gacgccaaua uuccauuaua    60
agau                                                                 64

<210> SEQ ID NO 15
<211> LENGTH: 67
<212> TYPE: DNA
<213> ORGANISM: Artificial Sequence
<220> FEATURE:
<223> OTHER INFORMATION: Synthetic DNA

<400> SEQUENCE: 15
cgccaatatt tacgtgctgc tacgccaata tttacgtgct gctacgccaa tatttacgtg    60
ctgctat                                                              67

<210> SEQ ID NO 16
```

```
<211> LENGTH: 64
<212> TYPE: DNA
<213> ORGANISM: Artificial Sequence
<220> FEATURE:
<223> OTHER INFORMATION: Synthetic DNA

<400> SEQUENCE: 16
cgccaatatt cgatgctgct acgccaatat tcgatgctgc tacgccaata ttcgatgctg    60
ctat                                                                 64

<210> SEQ ID NO 17
<211> LENGTH: 79
<212> TYPE: DNA
<213> ORGANISM: Artificial Sequence
<220> FEATURE:
<223> OTHER INFORMATION: Synthetic DNA

<400> SEQUENCE: 17
cgccaatatt tagttccgtg ctgctacgcc aatatttagt tccgtgctgc tacgccaata    60
tttagttccg tgctgctat                                                 79

<210> SEQ ID NO 18
<211> LENGTH: 79
<212> TYPE: DNA
<213> ORGANISM: Artificial Sequence
<220> FEATURE:
<223> OTHER INFORMATION: Synthetic DNA

<400> SEQUENCE: 18
cgccaatatt tagttccgtg ctgctacgcc aatatttagt tccgtgctgc tacgccaata    60
tttagttccg tgctgctat                                                 79

<210> SEQ ID NO 19
<211> LENGTH: 67
<212> TYPE: DNA
<213> ORGANISM: Artificial Sequence
<220> FEATURE:
<223> OTHER INFORMATION: Synthetic DNA

<400> SEQUENCE: 19
cgccaatatt tacgtaatta cacgccaata tttacgtaat tacacgccaa tatttacgta    60
attacat                                                              67
```

MICRO-RMA INHIBITOR

CROSS-REFERENCE TO RELATED APPLICATIONS

This patent application is the U.S. national phase of International Patent Application No. PCT/JP2013/055868, filed Mar. 4, 2013, which claims the benefit of Japanese Patent Application No. 2012-047466, filed on Mar. 4, 2012, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 4,790 bytes ASCII (Text) file named "718573SequenceListing.txt," created Sep. 2, 2014.

TECHNICAL FIELD

The present invention relates to a microRNA inhibitor.

BACKGROUND ART

MicroRNA is a small RNA of 18-25 mer, which is transcribed from the genome and regulates expression of the target gene. It is known that abnormal expression of microRNA is deeply involved in many diseases such as cancer and the like, and studies of microRNA as a target of diagnoses and treatments have been strenuously conducted in recent years. A method of inhibiting microRNA includes a method using LNA (Locked Nucleic Acid), and the method is in the clinical phase in Europe and the United States. As other inhibitory method of microRNA, there is a technique called microRNA Sponge (non-patent document 1).

DOCUMENT LIST

Non-Patent Document non-patent document 1: NATURE METHODS, 4:72

SUMMARY OF THE INVENTION

Problems to be Solved by the Invention

However, since a method using LNA requires use of a special modified nucleic acid, it lacks broad utility. Moreover, although microRNA Sponge has broad utility, it also has a problem in that RNA molecule is easily degraded by a degrading enzyme.

Accordingly, the present invention aims to provide a microRNA inhibitor having broad utility and difficult to degrade.

Means of Solving the Problems

To achieve the aforementioned object, the microRNA inhibitor of the present invention is characterized in that it has two or more sequences complementary to the sequence of microRNA to be the target of inhibition, and the aforementioned two or more complementary sequences are linked via a linker residue.

Effect of the Invention

Since the microRNA inhibitor of the present invention does not require use of a special modified nucleic acid, it is superior in broad utility, and difficult to degrade since the aforementioned complementary sequences are linked via a linker residue.

DESCRIPTION OF EMBODIMENTS

Figures 1, 2:
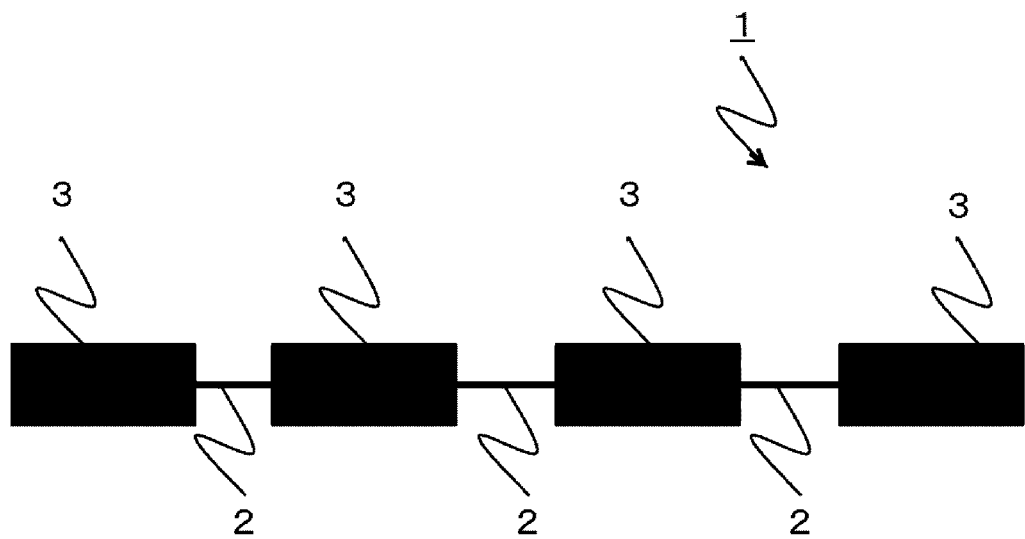
FIG. 1 shows an exemplary constitution of the microRNA inhibitor of the present invention.
FIG. 2 shows an exemplary sequence of the microRNA inhibitor of the present invention.

The present invention is explained in detail in the following by referring to examples. However, the present invention is not limited by the following explanations.

The microRNA inhibitor of the present invention preferably has a linker residue bonded to each terminal portion of the aforementioned complementary sequences present at the both termini of the microRNA inhibitor. With this form, degradation can be further suppressed.

In the microRNA inhibitor of the present invention, the aforementioned linker residue preferably contains at least one selected from the group consisting of an amino acid residue, a polyamine residue and a polycarboxylic acid residue. The aforementioned linker residue may or may not contain a residue other than the amino acid residue, polyamine residue and polycarboxylic acid residue. For example, the aforementioned linker residue may be any of a polycarboxylic acid residue, a terephthalic acid residue and an amino acid residue.

In the present invention, the "polyamine" means any compound containing a plurality of (two, three or more) amino groups. The aforementioned "amino group" is not limited to an —$NH_2$ group and also includes an imino group (—NH—). In the present invention, the aforementioned polyamine is not particularly limited, and examples thereof include 1,4-diaminobenzene, 1,3-diaminobenzene, 1,2-diaminobenzene and the like. In the present invention, moreover, the "polycarboxylic acid" means any compound containing a plurality of (two, three or more) carboxy groups. In the present invention, the aforementioned polycarboxylic acid is not particularly limited, and examples thereof include 1,4-dicarboxybenzene (terephthalic acid), 1,3-dicarboxybenzene (isophthalic acid), 1,2-dicarboxybenzene (phthalic acid) and the like. In the present invention, moreover, the "amino acid" means any organic compound containing one or more amino groups and one or more carboxy groups in a molecule, as mentioned below. The aforementioned "amino group" is not limited to an —$NH_2$ group and also includes an imino group (—NH—).

In the microRNA inhibitor of the present invention, the amino acid residue present between the aforementioned two or more complementary sequences may be a plurality of interlinked amino acid residues. In the present invention, the amino acid residue that is a plurality of interlinked amino acid residues is, for example, a residue containing a peptide structure. More specifically, the aforementioned amino acid residue that is a plurality of interlinked amino acid residues is, for example, an amino acid residue of the below-mentioned chemical formula (I) wherein the below-mentioned chemical formula (Ia) is a peptide (e.g., glycine dimer or glycine trimer etc.).

In the microRNA inhibitor of the present invention, the aforementioned amino acid residue may be a glycine residue, a terephthalamide residue or a proline residue.

In the microRNA inhibitor of the present invention, the amino acid residue bonded to the terminal portion of the aforementioned complementary sequence may be a plurality of interlinked amino acid residues. Also, in the microRNA inhibitor of the present invention, at least one of the aforementioned amino acid residue present between two or more complementary sequences and an amino acid residue bonded to the terminal portion of the aforementioned complementary sequence may be a residue of glycine dimer or trimer.

In the present invention, the aforementioned complementary sequence may be RNA or DNA.

In the present invention, the amino acid residue that links the aforementioned two or more complementary sequences is not particularly limited and, for example, glycine residue, terephthalamide residue or proline residue can be used as mentioned above. Also, the aforementioned amino acid residue may be a modified amino acid residue or an amino acid derivative. The amino acid residue that links (binds) the aforementioned two or more complementary sequences may be a single amino acid residue or two or more amino acid residues linked to each other.

In the present invention, as mentioned above, the aforementioned complementary sequences present at the both termini of a microRNA inhibitor preferably have the aforementioned linker residue linked to each terminal portion. The aforementioned linker residue may be, for example, an amino acid residue. While the aforementioned amino acid residue is not particularly limited, it is, for example, a glycine residue, a terephthalamide residue or a proline residue. The amino acid residue that links the aforementioned two or more complementary sequences may be a single amino acid residue or two or more amino acid residues.

In the present invention, the aforementioned complementary sequence is complementary to the whole or a part of microRNA to be the target of inhibition. When the sequence is partially complementary, it is preferably complementary to a sequence on the 3' side or 5' side from the loop of microRNA. The aforementioned complementary sequence may contain a sequence complementary to the whole or a part of the loop part of microRNA. The number of the aforementioned complementary sequence is two or more, for example, 2-10, preferably 3-8, more preferably 4-6. While the base number of the aforementioned complementary sequence is not particularly limited, it may be, for example, about 20-25 bases. The aforementioned complementary sequence may be RNA or DNA, as mentioned above, or may be a mixture of DNA and RNA. The nucleic acid constituting the aforementioned complementary sequence is preferably a natural nucleic acid. However, the present invention is not limited thereto and it may be, for example, a modified nucleic acid. In addition, a nucleic acid constituting the aforementioned complementary sequence may be, for example, artificial nucleic acid such as LNA (BNA), PNA and the like. From the aspects of broad utility and convenience, a natural nucleic acid is preferable, as mentioned above.

An example of the constitution of the microRNA inhibitor of the present invention is shown in FIG. 1. As shown in this Figure, in the microRNA inhibitor 1 of this example, three complementary sequences 2 are linked via two linker residues (e.g., amino acid residue) 3, and the linker residue 3 is also linked to each terminal portion of complementary sequences 2 at both ends. Also, an example of the sequence of the microRNA inhibitor of the present invention when hsa-miR-15a as microRNA is the target of inhibition is shown in FIG. 2. In this example, the aforementioned complementary sequence (SEQ ID NO: 1) is complementary to the full-length sequence of hsa-miR-15a.

```
5'-CACAAACCATGCCTGCTGCTA-3'     (SEQ ID NO: 1)
```

Figure 3:
FIG. 3 schematically shows an example of a mismatch sequence.
Figure 3:
Figure 3:

In the microRNA inhibitor of the present invention, the aforementioned complementary sequence may be completely complementary (full match) to, for example, the whole or part of microRNA, or may contain a mismatch. When the microRNA inhibitor of the present invention contains a mismatch, cleavage by an enzyme (Dicer etc.) that cleaves double stranded nucleic acid is suppressed, and degradation preferably becomes more difficult. The aforementioned mismatch is not particularly limited. For example, a mismatch of 1 base-several bases may be present in the center of the aforementioned complementary sequence, or the center of the aforementioned complementary sequence may be a Bulge (in addition to complementary sequence for the target sequence, containing an extra-sequence of 1 base-several bases [for example, about 4 bases] in the center). The aforementioned "center" of the aforementioned complementary sequence is not particularly limited as long as it is other than the base at the terminus of the aforementioned complementary sequence. FIG. 3 schematically shows an example of mismatch together with an example of full match. FIG. 3(a) is a schematic showing of an example of the full match, FIG. 3(b) is a schematic showing of an example of the aforementioned Bulge, and FIG. 3(c) is a schematic showing of an example of the aforementioned complementary sequence having a mismatch of 1 base-several bases in the center thereof. In each of FIG. 3(a)-(c), the white chain on the lower side shows a target sequence (whole or part of microRNA), and the black chain on the upper side shows the aforementioned complementary sequence. Examples of the mismatch of FIGS. 3(b) and (c) (particularly, FIG. 3(c)) are sometimes referred to as Bubble type and the like. Alternatively, the example of the full match of FIG. 3(a) is sometimes referred to as Perfect type, the example of FIG. 3(b) is sometimes referred to as Bulge type, and the example of FIG. 3(c) is sometimes referred to as Bubble type.

The microRNA inhibitor of the present invention can be produced by, for example, chemical synthesis as shown below.

The aforementioned chemical synthesis method is not particularly limited, and examples thereof include phosphoramidite method, H-phosphonate method and the like. In the aforementioned chemical synthesis method, for example, a commercially available automatic nucleic acid synthesizer can be used. In the aforementioned chemical synthesis method, for example, an amidite can be used. The aforementioned amidite is not particularly limited, and examples of the commercially available amidite include RNA Phosphoramidites (2'-O-TBDMSi, trade name, Samchully Pharm Co., Ltd.), ACE amidite, TOM amidite, CEE amidite, CEM amidite, TEM amidite and the like. The microRNA inhibitor of the present invention preferably uses, for example, in the synthesis of the aforementioned amino acid residue, the below-mentioned monomer of the present invention.

In the microRNA inhibitor of the present invention, the aforementioned linker residue is represented by, for example, the following chemical formula (I-0)

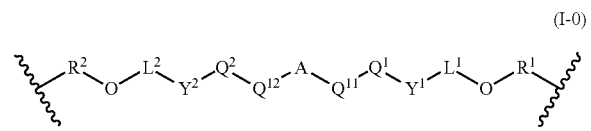

(I-0)

in the aforementioned chemical formula (I-0),
$Q^{11}$ and $Q^{12}$ are each independently a single bond, $CH_2$ (a methylene group), NH (an imino group), C=O (a carbonyl group), C=S (a thiocarbonyl group), C=NH (an iminomethylene group), O, or S,
$Q^1$ and $Q^2$ are each independently a single bond, $CH_2$ (a methylene group), NH (an imino group), C=O (a carbonyl group), C=S (a thiocarbonyl group), C=NH (an iminomethylene group), O, or S, $Y^1$ and $Y^2$ are each independently a single bond, $CH_2$, NH, O, or S;
$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or,
$L^1$ is a polyether chain obtained by substituting at least one carbon atom on the aforementioned alkylene chain with an oxygen atom,
provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or
$L^2$ is a polyether chain obtained by substituting at least one carbon atom on the aforementioned alkylene chain with an oxygen atom,
provided that: when $Y^2$ is NH, O, or S, an atom bound to $Y^2$ in $L^2$ is carbon, an atom bound to $OR^2$ in $L^2$ is carbon, and oxygen atoms are not adjacent to each other;
$R^a$, $R^b$, $R^c$, and $R^d$ are each independently a substituent or a protecting group;
m is an integer in the range from 0 to 30;
n is an integer in the range from 0 to 30;
a sequence complementary to the sequence of the aforementioned microRNA is bound to the aforementioned linker residue each via $—OR^1—$ or $—OR^2—$,
when the aforementioned linker residue is present between the complementary sequences of the aforementioned microRNA, $R^1$ and $R^2$ may or may not be present, and when they are present, $R^1$ and $R^2$ are each independently a nucleotide residue or the aforementioned structure (I-0);
when the aforementioned linker residue is present at the terminal portion of the complementary sequence of the aforementioned microRNA present at the terminus, $R^1$ and $R^2$ are each independently H, a protecting group or a phosphate-protecting group; and
A is any atomic group.

In the aforementioned chemical formula (I-0), for example, $Q^{11}$ may be C=O (a carbonyl group), and $Q^1$ may be NH (an imino group). In addition, for example, $Q^{11}$ may be NH (an imino group), and $Q^1$ may be C=O (a carbonyl group). Furthermore, for example, $Q^{12}$ may be C=O (a carbonyl group), and $Q^2$ may be NH (an imino group). Moreover, for example, $Q^{12}$ may be NH (an imino group), and $Q^2$ may be C=O (a carbonyl group).

In the aforementioned chemical formula (I-0), each of $Q^{11}$ and $Q^{12}$ may be, for example, a carbonyl group. In this case, each of $Q^1$ and $Q^2$ is preferably an imino group. In addition, in this case, the structure of the following chemical formula (Iα) is more preferably represented by the following chemical formula (Iα2).

(Iα)

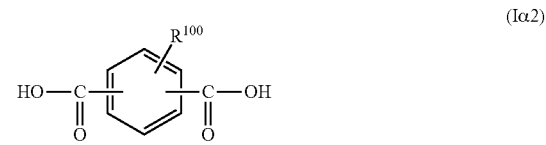

(Iα2)

In the aforementioned chemical formula (Iα2),
$R^{100}$ is any substituent, which may or may not be present. When it is present, it may be present singly or in plurality. When it is present in plurality, they may be the same or different from each other. Examples of the aforementioned any substituent for $R^{100}$ include the below-mentioned substituents exemplified as the aforementioned $R^a$, $R^b$, $R^c$ and $R^d$. More specific examples thereof include halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl and the like. The structure of the aforementioned chemical formula (Iα2) is more preferably represented by the following chemical formula (Iα3).

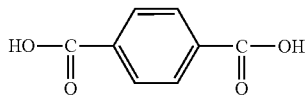

When $Q^{11}$ and $Q^{12}$ are carbonyl groups, and $Q^1$ and $Q^2$ are imino groups, the linker residue of the aforementioned chemical formula (I-0) can be a carboxylic acid amide residue or a carboxylic acid residue. For example, the "TPA" structure in the below-mentioned Example can be a terephthalamide residue or a terephthalic acid residue represented by the aforementioned chemical formula (Iα3).

In the aforementioned chemical formula (I-0), each of $Q^{11}$ and $Q^{12}$ may be an imino group. In this case, each of $Q^1$ and $Q^2$ is preferably a carbonyl group. In this case, the structure of the following chemical formula (Iβ) is more preferably represented by the following chemical formula (Iβ2).

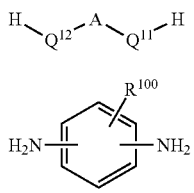

In the aforementioned chemical formula (Iβ2),
$R^{100}$ is any substituent, which may or may not be present. When it is present, it may be present singly or in plurality. When it is present in plurality, they may be the same or different from each other. Specifically, for example, it is the same as $R^{100}$ in the aforementioned chemical formula (Iα2). In addition, the structure of the aforementioned chemical formula (Iβ2) is more preferably represented by the following chemical formula (Iβ3).

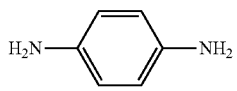

In the microRNA inhibitor of the present invention, when the aforementioned linker residue is an amino acid residue, the aforementioned amino acid residue is represented by, for example, the following chemical formula (I). The structure of the following chemical formula (I) is one example of the structure represented by the aforementioned chemical formula (I-0)

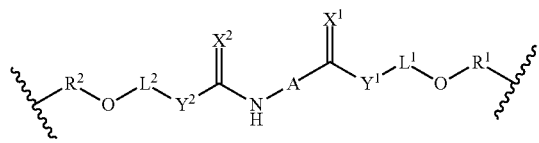

In the aforementioned chemical formula (I), for example, $X^1$ and $X^2$ are each independently $H_2$, O, S, or NH;

$Y^1$ and $Y^2$ are each independently a single bond, $CH_2$, NH, O, or S;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

the sequence complementary to the sequence of the aforementioned microRNA is each bound to the aforementioned amino acid residue via $—OR^1—$ or $—OR^2—$, when the aforementioned amino acid residue is present between the complementary sequences of the aforementioned microRNA, $R^1$ and $R^2$ may or may not be present, and when they are present, $R^1$ and $R^2$ are each independently a nucleotide residue or the aforementioned structure (I);

when the aforementioned amino acid residue is present at the terminal portion of the complementary sequence of the aforementioned microRNA present at the terminus, $R^1$ and $R^2$ are each independently H, a protecting group or a phosphate-protecting group; and A is any atomic group, the following chemical formula (Ia) is an amino acid or peptide.

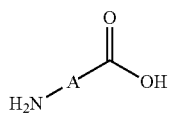

In the aforementioned chemical formula (I), for example, $X^1$ and $X^2$ are each independently $H_2$, O, S, or NH. In the aforementioned chemical formula (I), "$X^1$ is $H_2$" means that $X^1$ forms $CH_2$ (a methylene group) together with a carbon atom to which $X^1$ binds. The same applies to $X^2$.

In the aforementioned chemical formula (I), $Y^1$ and $Y^2$ are each independently a single bond, $CH_2$, NH, O, or S.

In the aforementioned chemical formulas (I-0) and (I), $L^1$ is an alkylene chain having n carbon atoms. A hydrogen atom(s) on the aforementioned alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the aforementioned alkylene chain with an oxygen atom. The aforementioned polyether chain is, for example, polyethylene glycol. When $Y^1$ is NH, O, or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the aforementioned chemical formulas (I-0) and (I), $L^2$ is an alkylene chain having m carbon atoms. A hydrogen atom(s) on the aforementioned alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the aforementioned alkylene chain with an oxygen atom. When $Y^2$ is NH, O, or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. For example, n and m can be set as appropriate depending on a desired length of the aforementioned amino acid residue. For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

For example, $R^a$, $R^b$, $R^c$ and $R^d$ are each independently a substituent or a protecting group, and may be the same or different. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino [alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like. These substituents are optionally substituted by one or more further substituents or further protecting groups. While the aforementioned further substituent is not particularly limited, for example, it may be a substituent exemplified above. The aforementioned further protecting group is not particularly limited and, for example, it may be a protecting group exemplified below. The same applies hereafter.

The aforementioned protecting group (or the aforementioned further protecting group) is a functional group that inactivates, for example, a highly-reactive functional group. Examples of the protecting group include known protecting groups. Regarding the aforementioned protecting group, for example, the description in the literature (J. F. W. McOmie, "Protecting Groups in Organic Chemistry", Plenum Press, London and New York, 1973) can be incorporated herein. The aforementioned protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). Other examples of the protecting group include silyl-containing groups represented by the chemical formulae (P1) and (P2) to be shown later. The same applies hereinafter.

In the aforementioned chemical formulas (I-0) and (I), a hydrogen atoms each independently may be substituted with, for example, a halogen such as F, Cl, Br, or I.

In the microRNA inhibitor of the present invention, the aforementioned complementary sequence is each bound to the aforementioned linker residue (e.g., amino acid residue) via, for example, $-OR^1-$ or $-OR^2-$. $R^1$ and $R^2$ may or may not be present. When $R^1$ and $R^2$ are present, $R^1$ and $R^2$ may be each independently a nucleotide residue or the structure represented by the aforementioned chemical formula (I-0) or (I). When $R^1$ and/or $R^2$ are/is the aforementioned nucleotide residue, the aforementioned linker residue (e.g., amino acid residue) is composed of, for example, the aforementioned non-nucleotide residue having the structure of the aforementioned chemical formula (I-0) or (I) excluding the nucleotide residue $R^1$ and/or $R^2$, and the aforementioned nucleotide residue(s). When $R^1$ and/or $R^2$ are/is the structure represented by the aforementioned chemical formula (I-0) or (I), the structure of the aforementioned linker residue (e.g., amino acid residue) is such that, for example, two or more of the aforementioned non-nucleotide residues having the structure of the aforementioned chemical formula (I-0) or (I) are linked to each other. The number of the structures of the aforementioned chemical formula (I-0) or (I) may be, for example, 1, 2, 3, or 4. When the linker residue (e.g., amino acid residue) includes a plurality of the aforementioned structures, the structures of the aforementioned chemical formula (I-0) or (I) may be linked, for example, either directly or via the aforementioned nucleotide residue(s). On the other hand, when $R^1$ and $R^2$ are not present, the aforementioned linker residue (e.g., amino acid residue) is composed of, for example, the aforementioned non-nucleotide residue having the structure of the aforementioned chemical formula (I-0) or (I) alone.

In the present invention, the atomic group A in the aforementioned chemical formula (I) is not particularly limited and is arbitrarily chosen; however, the following chemical formula (Ia) shows an amino acid or a peptide, as mentioned above.

(Ia)

The atomic group A in the aforementioned chemical formula (I), (IA) or (Ia) may or may not contain, for example, at least one selected from the group consisting of chain atomic group, alicyclic atomic group, aromatic atomic group, heteroaromatic atomic group and heteroalicyclic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. The aforementioned heteroaromatic atomic group is not particularly limited, and examples thereof include heteroaryl, heteroarylalkyl, alkylheteroaryl, condensed cyclic heteroaryl, condensed cyclic heteroarylalkyl, condensed cyclic alkylheteroaryl and the like. In the atomic group A in the aforementioned chemical formula (I), (IA) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to any organic compound containing at least one amino group and at least one carboxy group in a molecule, as mentioned above. The aforementioned "amino group" is not limited to an —$NH_2$ group and also includes an imino group (—NH—). For example, proline, hydroxyproline and the like do not contain an —$NH_2$ group in a molecule, but contains an imino group (—NH—), and is included in the definition of the "amino acid" in the present invention. In the present invention, the aforementioned "amino acid" may be, as mentioned below, a natural amino acid or an artificial amino acid. For example, a compound represented by the below-mentioned chemical formula (Ia2) or (Ia3) also contains an amino group and a carboxy group in the molecule, and therefore, it is included in the definition of the "amino acid" in the present invention. Therefore, for example, the structure of the aforementioned chemical formula (I), wherein atomic group A is represented by the below-mentioned chemical formula (A2) or chemical formula (A2a), is included in the definition of the "amino acid residue" in the present invention. In addition, for example, the "TPA" structure in the below-mentioned Example is also included in the definition of the "amino acid residue" in the present invention. In the present invention, moreover, the "peptide" refers to an organic compound having a structure wherein not less than 2 molecules of amino acid are bonded via a peptide bond. The aforementioned peptide bond may be an acid amide structure or an acid imide structure. When plural amino groups are present in the amino acid or peptide molecule represented by the aforementioned chemical formula (Ia), the amino group clearly shown in the aforementioned chemical formula (Ia) may be any amino group. In addition, when plural carboxy groups are present in the amino acid or peptide molecule represented by the aforementioned chemical formula (Ia), the carboxy group clearly shown in the aforementioned chemical formula (Ia) may be any carboxy group.

In the aforementioned amino acid residue of the microRNA inhibitor of the present invention, the aforementioned amino acid may be, for example, as mentioned above, natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a heterocycle. The aforementioned amino acid may be an amino acid constituting, for example, a protein. The aforementioned amino acid may be, for example, at least one kind selected from the group consisting of glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid and amino acid represented by the following chemical formula (Ia2), and may or may not further have a substituent or a protecting group. Examples of the aforementioned substituent include the substituents exemplified for the aforementioned $R^a$, $R^b$, $R^c$ and $R^d$. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned $R^a$, $R^b$, $R^c$ and $R^d$. When the amino acid of the aforementioned chemical formula (Ia), which is not peptide, contains isomers such as optical isomer, geometric isomer, stereoisomer and the like, any isomer can be used.

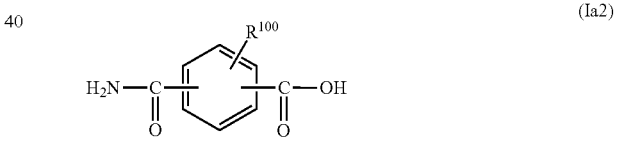

(Ia2)

In the aforementioned chemical formula (Ia2), $R^{100}$ is any substituent, and may or may not be present. When it is present, it may be present singly or in plurality. When it is present in plurality, they may be the same or different from each other. Examples of the aforementioned any substituent for $R^{100}$ include those exemplified as the aforementioned $R^a$, $R^b$, $R^c$ or $R^d$. More specific examples thereof include halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. In addition, the structure of the aforementioned chemical formula (Ia2) may be, for example, the following chemical formula (Ia3).

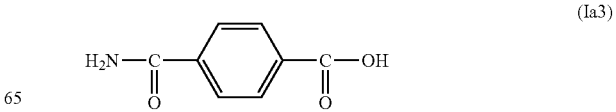

(Ia3)

When the structure of the aforementioned chemical formula (Ia) is the aforementioned chemical formula (Ia2), the structure of atomic group A in the aforementioned chemical formula (I) is represented by the following chemical formula (A2). $R^{100}$ in the following chemical formula (A2) is the same as $R^{100}$ in the aforementioned chemical formula (Ia2). In addition, when the structure of the aforementioned chemical formula (Ia) is the aforementioned chemical formula (Ia3), the structure of atomic group A in the aforementioned chemical formula (I) is represented by the following chemical formula (A2a).

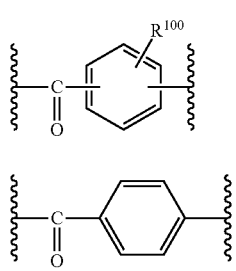

(A2)

(A2a)

Examples of the structure of the aforementioned chemical formula (I) include the following chemical formulas (I-1)-(I-6). In the following chemical formulas (I-1)-(I-6), n and m are the same as in the aforementioned chemical formula (I).

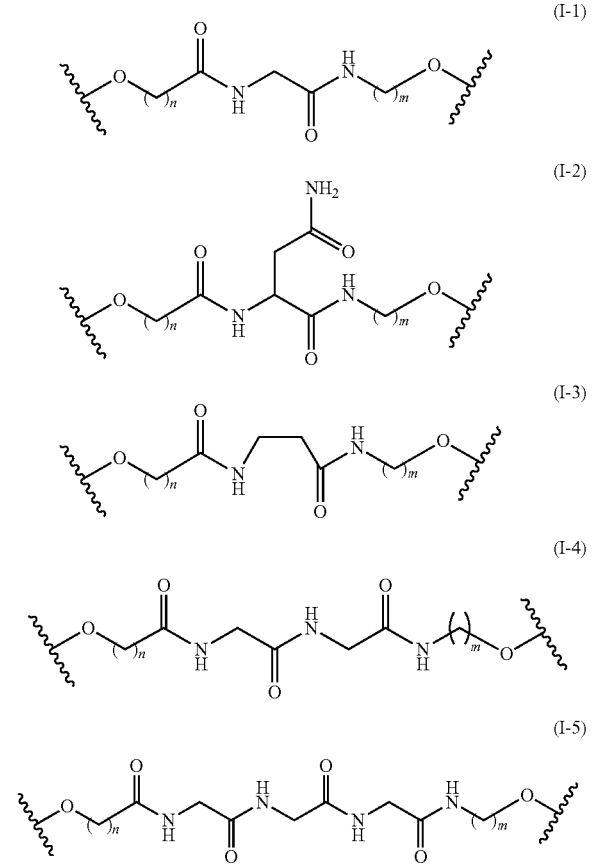

(I-1)

(I-2)

(I-3)

(I-4)

(I-5)

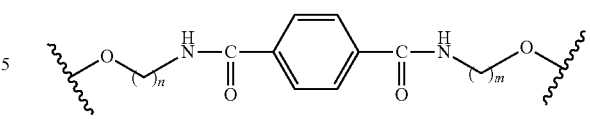

(I-6)

In the aforementioned chemical formulae (I-1) to (I-6), n and m are not particularly limited, and are as described above. Specific examples thereof include n=11 and m=12 in the aforementioned chemical formula (I-1), n=5 and m=4 in the aforementioned chemical formula (I-4), and n=4 and m=4 in the aforementioned chemical formula (I-6). The structures are shown by the following chemical formulas (I-1a), (I-4-a) and (I-6a).

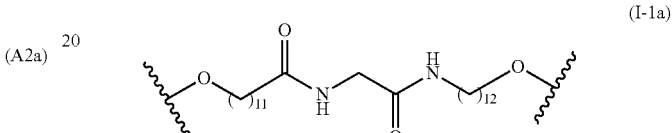

(I-1a)

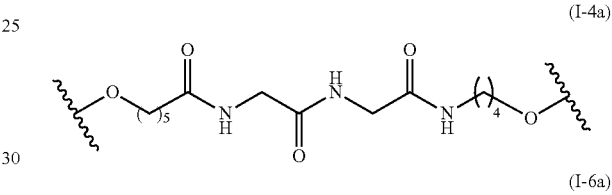

(I-4a)

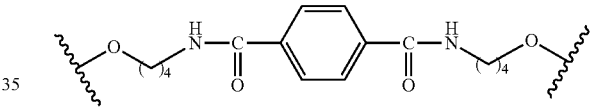

(I-6a)

In the present invention, "alkyl" includes, for example, linear or branched alkyl group. The carbon number of the aforementioned alkyl is not particularly limited and, for example, 1-30, preferably 1-6, more preferably 1-4. Examples of the aforementioned alkyl group include methyl, ethyl, n-propyl, isopropyl, n-butyl, isobutyl, sec-butyl and tert-butyl, n-pentyl, isopentyl, neopentyl, n-hexyl, isohexyl, n-heptyl, n-octyl, n-nonyl, n-decyl and the like. Preferably, for example, methyl, ethyl, n-propyl, isopropyl, n-butyl, isobutyl, sec-butyl, tert-butyl, n-pentyl, isopentyl, neopentyl, n-hexyl, isohexyl and the like can be mentioned.

In the present invention, "alkenyl" includes, for example, linear or branched alkenyl. The aforementioned alkenyl is, for example, the aforementioned alkyl containing one or plural double bonds and the like. The carbon number of the aforementioned alkenyl is not particularly limited and, for example, the same as for the aforementioned alkyl and preferably 2-8. Examples of the aforementioned alkenyl include vinyl, 1-propenyl, 2-propenyl, 1-butenyl, 2-butenyl, 3-butenyl, 1,3-butadienyl, 3-methyl-2-butenyl and the like.

In the present invention, "alkynyl" includes, for example, linear or branched alkynyl. The aforementioned alkynyl is, for example, the aforementioned alkyl containing one or plural triple bonds and the like. The carbon number of the aforementioned alkynyl is not particularly limited and, for example, the same as for the aforementioned alkyl and preferably 2-8. Examples of the aforementioned alkynyl include ethynyl, propynyl, butynyl and the like. The aforementioned alkynyl may further have, for example, one or plural double bonds.

In the present invention, "aryl" includes, for example, a monocyclic aromatic hydrocarbon group and a polycyclic aromatic hydrocarbon group. Examples of the aforementioned monocyclic aromatic hydrocarbon group include phenyl and the like. Examples of the aforementioned polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl and the like. Preferably, for example, phenyl, naphthyl such as 1-naphthyl and 2-naphthyl and the like, and the like can be mentioned.

In the present invention, "heteroaryl" includes, for example, a monocyclic aromatic heterocyclic group and a fused aromatic heterocyclic group. Examples of the aforementioned heteroaryl include furyl (e.g., 2-furyl, 3-furyl), thienyl (e.g., 2-thienyl, 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1,2,4-triazol-1-yl, 1,2,4-triazol-3-yl, 1,2,4-triazol-4-yl), tetrazolyl (e.g., 1-tetrazolyl, 2-tetrazolyl, 5-tetrazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), thiadiazolyl, isothiazolyl (e.g., 3-isothiazolyl, 4-isothiazolyl, 5-isothiazolyl), pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), furazanyl (e.g., 3-furazanyl), pyrazinyl (e.g., 2-pyrazinyl), oxadiazolyl (e.g., 1,3,4-oxadiazol-2-yl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyl (e.g., 1-benzimidazolyl, 2-benzimidazolyl, 4-benzimidazolyl, 5-benzimidazolyl), dibenzofuryl, benzoxazolyl, benzothiazolyl, quinoxalyl (e.g., 2-quinoxalinyl, 5-quinoxalinyl, 6-quinoxalinyl), cinnolinyl (e.g., 3-cinnolinyl, 4-cinnolinyl, 5-cinnolinyl, 6-cinnolinyl, 7-cinnolinyl, 8-cinnolinyl), quinazolyl (e.g., 2-quinazolinyl, 4-quinazolinyl, 5-quinazolinyl, 6-quinazolinyl, 7-quinazolinyl, 8-quinazolinyl), quinolyl (e.g., 2-quinolyl, 3-quinolyl, 4-quinolyl, 5-quinolyl, 6-quinolyl, 7-quinolyl, 8-quinolyl), phthalazinyl (e.g., 1-phthalazinyl, 5-phthalazinyl, 6-phthalazinyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), puryl, pteridinyl (e.g., 2-pteridinyl, 4-pteridinyl, 6-pteridinyl, 7-pteridinyl), carbazolyl, phenanthridinyl, acridinyl (e.g., 1-acridinyl, 2-acridinyl, 3-acridinyl, 4-acridinyl, 9-acridinyl), indolyl (e.g., 1-indolyl, 2-indolyl, 3-indolyl, 4-indolyl, 5-indolyl, 6-indolyl, 7-indolyl), isoindolyl, phenazinyl (e.g., 1-phenazinyl, 2-phenazinyl) or phenothiazinyl (e.g., 1-phenothiazinyl, 2-phenothiazinyl, 3-phenothiazinyl, 4-phenothiazinyl) and the like.

In the present invention, "cycloalkyl" is, for example, a cyclic saturated hydrocarbon group, and the carbon number is, for example, 3-15. Examples of the aforementioned cycloalkyl include cyclopropyl, cyclobutyl, cyclopentyl, cyclohexyl, cycloheptyl, cyclooctyl, bridged cyclic hydrocarbon group, so spiro hydrocarbon group and the like, preferably, cyclopropyl, cyclobutyl, cyclopentyl, cyclohexyl, bridged cyclic hydrocarbon group and the like.

In the present invention, the "bridged cyclic hydrocarbon group" is, for example, bicyclo[2.1.0]pentyl, bicyclo[2.2.1]heptyl, bicyclo[2.2.2]octyl and bicyclo[3.2.1]octyl, tricyclo[2.2.1.0]heptyl, bicyclo[3.3.1]nonane, 1-adamantyl, 2-adamantyl or the like.

In the present invention, the "spiro hydrocarbon group" is, for example, spiro[3.4]octyl or the like.

In the present invention, "cycloalkenyl" includes, for example, a cyclic unsaturated aliphatic hydrocarbon group, and the carbon number is, for example, 3-7. Examples of the aforementioned cycloalkenyl include cyclopropenyl, cyclobutenyl, cyclopentenyl, cyclohexenyl, cycloheptenyl and the like, preferably, cyclopropenyl, cyclobutenyl, cyclopentenyl, cyclohexenyl and the like. The aforementioned cycloalkenyl includes, for example, a bridged cyclic hydrocarbon group and a spiro hydrocarbon group having an unsaturated bond in the ring.

In the present invention, "arylalkyl" is, for example, benzyl, 2-phenethyl, naphthalenylmethyl or the like, "cycloalkylalkyl" or "cyclylalkyl" is, for example, cyclohexylmethyl, adamantylmethyl or the like, and "hydroxyalkyl" is, for example, hydroxymethyl and 2-hydroxyethyl or the like.

In the present invention, "alkoxy" includes, for example, the aforementioned alkyl-O— group and, for example, methoxy, ethoxy, n-propoxy, isopropoxy, n-butoxy and the like can be mentioned, and "alkoxyalkyl" is, for example, methoxymethyl or the like, and "aminoalkyl" is, for example, 2-aminoethyl or the like.

In the present invention, "heterocyclyl" is, for example, 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazolinyl, 4-imidazolinyl, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, tetrahydrofuranyl or the like.

In the present invention, "heterocyclylalkyl" includes, for example, piperidinylmethyl, piperazinylmethyl and the like, "heterocyclylalkenyl" includes, for example, 2-piperidinylethenyl and the like, and "heteroarylalkyl" includes, for example, pyridylmethyl, quinolin-3-ylmethyl and the like.

In the present invention, "silyl" includes a group represented by the chemical formula $R_3Si-$, wherein R can be, independently, selected from the aforementioned alkyl, aryl and cycloalkyl and, for example, a trimethylsilyl group, a tert-butyldimethylsilyl group and the like can be mentioned. The "silyloxy" is, for example, a trimethylsilyloxy group and the like, and "silyloxyalkyl", for example, trimethylsilyloxymethyl or the like.

In the present invention, "alkylene" is, for example, methylene, ethylene, propylene or the like.

In the present invention, the aforementioned various groups are optionally substituted. Examples of the aforementioned substituent include hydroxy, carboxy, sulfo, halogen, alkyl halide (haloalkyl, e.g., $CF_3$, $CH_2CF_3$, $CH_2CCl_3$), nitro, nitroso, cyano, alkyl (e.g., methyl, ethyl, isopropyl, tert-butyl), alkenyl (e.g., vinyl), alkynyl (e.g., ethynyl), cycloalkyl (e.g., cyclopropyl, adamantyl), cycloalkylalkyl (e.g., cyclohexylmethyl, adamantylmethyl), cycloalkenyl (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryl (e.g., phenyl, naphthyl), arylalkyl (e.g., benzyl, phenethyl), alkylaryl (e.g., p-methylphenyl), heteroaryl (e.g., pyridyl, furyl), heteroarylalkyl (e.g., pyridylmethyl), heterocyclyl (e.g., piperidyl), heterocyclylalkenyl, heterocyclylalkyl (e.g., morpholylmethyl), alkoxy (e.g., methoxy, ethoxy, propoxy, butoxy), halogenated alkoxy (e.g., $OCF_3$), alkenyloxy (e.g., vinyloxy, allyloxy), aryloxy (e.g., phenyloxy), alkyloxycarbonyl (e.g., methoxycarbonyl, ethoxycarbonyl, tert-butoxycarbonyl), arylalkyloxy (e.g., benzyloxy), amino[alkylamino (e.g., methylamino, ethylamino, dimethylamino), acylamino (e.g., acetylamino, benzoylamino), arylalkylamino (e.g., benzylamino, tritylamino), hydroxyamino], aminoalkyl (e.g., aminomethyl), alkylaminoalkyl (e.g., diethylaminomethyl), carbamoyl, sulfamoyl, oxo, silyl, silyloxyalkyl and the like.

In the present invention, a molecule for introduction of the aforementioned linker residue (hereinafter to be referred to as "the monomer of the present invention" or simply "monomer") optionally has, for example, the structure of the following chemical formula (II-0). Unless particularly indicated, the explanation on the linker residue represented by the aforementioned chemical formula (I-0) can be quoted for the monomer of the present invention having the structure of the following chemical formula (II-0).

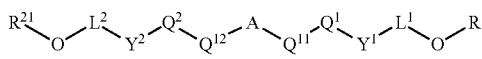

(II-0)

In the aforementioned chemical the formula (II-0), $Q^{11}$ and $Q^{12}$ are each independently a single bond, $CH_2$ (a methylene group), NH (an imino group), C=O (a carbonyl group), C=S (a thiocarbonyl group), C=NH (an iminomethylene group), O or S, $Q^1$ and $Q^2$ are each independently a single bond, $CH_2$ (methylene group), NH (an imino group), C=O (a carbonyl group), C=S (a thiocarbonyl group), C=NH (an iminomethylene group), O or S, $Y^1$ and $Y^2$ are each independently a single bond, $CH_2$, NH, O or S; $R^{11}$ and $R^{21}$ are each independently H, a protecting group or a phosphate-protecting group;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in L is carbon, an atom bound to $OR^{11}$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^{21}$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30; and

A is any atomic group.

The monomer of the present invention (molecule for introduction of the aforementioned linker residue) optionally has, for example, the structure of the following chemical formula (II). Unless particularly indicated, the explanation on the linker residue (amino acid residue) represented by the aforementioned chemical formula (I) can be quoted for the monomer of the present invention having the structure of the following chemical formula (II).

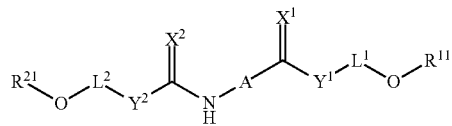

(II)

In the aforementioned chemical formula (II), $X^1$ and $X^2$ are each independently $H_2$, O, S, or NH;

$Y^1$ and $Y^2$ are each independently a single bond, $CH_2$, NH, O, or S;

$R^{11}$ and $R^{21}$ are each independently H, a protecting group or a phosphate-protecting group;

$L^1$ is an alkylene chain having n carbon atoms, and a hydrogen atom on an alkylene carbon atom may or may not be substituted with OH, $OR^a$, $NH_2$, $NHR^a$, $NR^aR^b$, SH, or $SR^a$, or, $L^1$ is a polyether chain obtained by substituting at least one carbon atom on the aforementioned alkylene chain with an oxygen atom, provided that: when $Y^1$ is NH, O, or S, an atom bound to $Y^1$ in $L^1$ is carbon, an atom bound to $OR^{11}$ in $L^1$ is carbon, and oxygen atoms are not adjacent to each other;

$L^2$ is an alkylene chain having m carbon atoms, and a hydrogen atom on an alkylene carbon atom may or may not be substituted with OH, $OR^c$, $NH_2$, $NHR^c$, $NR^cR^d$, SH, or $SR^c$, or $L^2$ is a polyether chain obtained by substituting at least one carbon atom on the aforementioned alkylene chain with an oxygen atom, provided that: when $Y^2$ is NH, O, or S, an atom bound to $Y^2$ in $L^2$ is carbon, an atom bound to $OR^{21}$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

A is any atomic group, the following chemical formula (Ia) is an amino acid or a peptide.

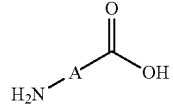

(Ia)

By use of the monomer of the present invention represented by the aforementioned chemical formula (II-0) or (II), for example, in the synthesis of the microRNA inhibitor of the present invention, the amino acid residue represented by the aforementioned chemical formula (I-0) or (I) can be synthesized easily. The monomer of the present invention can be used an amidite for automated nucleic acid synthesis, for example, in the synthesis of the microRNA inhibitor of the present invention, and is applicable to, for example, general automated nucleic acid synthesizers. Examples of the aforementioned synthesis method include a phosphoramidite method and an H— phosphonate method.

In the aforementioned chemical formula (II-0) or (II), the explanation on the aforementioned chemical formula (I-0) or (I) can be quoted for the same portion as in the aforementioned chemical formula (I-0) or (I). Specifically, in the aforementioned chemical formula (II-0) or (II), for example, the explanation on the aforementioned chemical formula (I-0) or (I) can be quoted for $X^1$, $X^2$, $Y^1$, $Y^2$, $L^1$, $L^2$, m, n and A.

In the aforementioned chemical formula (II-0) or (II), $R^{11}$ and $R^{21}$ are, as mentioned above, each independently H, a protecting group or a phosphate-protecting group.

The explanation on the aforementioned protecting groups is the same as in, for example, the aforementioned chemical formula (I-0) or (I), and specific examples thereof can be selected from, for example, the following group I. The aforementioned group I includes DMTr group, TBDMS group, ACE group, TOM group, CEE group, CEM group, TEM group, and silyl-containing group represented by the following chemical formula (P1) or (P2). The aforementioned protecting group is particularly preferably any of DMtr group and the aforementioned silyl-containing group.

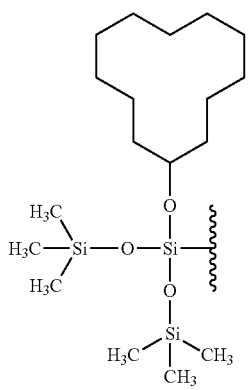

(P1)

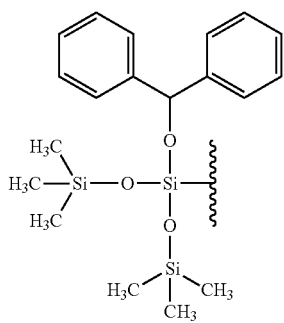

(P2)

The aforementioned phosphate-protecting group can be represented, for example, by the following chemical formula:

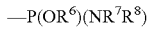

(P3)

In the aforementioned chemical formula (P3), $R^6$ is a hydrogen atom or any substituent. For example, the substituent $R^6$ is preferably a hydrocarbon group, and the aforementioned hydrocarbon group may or may not be substituted with an electron-withdrawing group. Examples of the substituent $R^6$ include halogens, haloalkyls, heteroaryls, hydroxyalkyls, alkoxyalkyls, aminoalkyls, silyls, silyloxyalkyls, heterocyclylalkenyls, heterocyclylalkyls, heteroarylalkyls, and hydrocarbons such as alkyls, alkenyls, alkynyls, aryls, arylalkyls, cycloalkyls, cycloalkenyls, cycloalkylalkyls, and cyclylalkyls, which may or may not be substituted with an electron-withdrawing group. Specific examples of the substituent $R^6$ include a β-cyanoethyl group, a nitrophenylethyl group, and a methyl group.

$R^7$ and $R^8$ are each a hydrogen atom or any substituent, and they may be the same or different. The substituents $R^7$ and $R^8$ are preferably, for example, hydrocarbon groups, and the aforementioned hydrocarbon group may or may not be further substituted with any substituent. Examples of the is aforementioned hydrocarbon group are the same as those listed in the above description regarding $R^6$, and the hydrocarbon group is preferably a methyl group, an ethyl group, or an isopropyl group. In this case, specific examples of —$NR^7R^8$ include a diisopropylamino group, a diethylamino group, and an ethylmethylamino group. Alternatively, the substituents $R^7$ and $R^8$ are joined to optionally form, together with the nitrogen atom (s) bonded thereto (i.e., —$NR^7R^8$ as a whole), a nitrogen-containing ring (e.g., a piperidyl group, a morpholino group, or the like).

Specific examples of the phosphate-protecting group represented by the aforementioned chemical formula (P3) include those selected from the following group II. Group II consists of —$P(OCH_2CH_2CN)$ $(N(i-Pr)_2)$ and —$P(OCH_3)$ $(N(i-Pr)_2)$. In the aforementioned chemical formula, i-Pr is isopropyl.

In the aforementioned chemical formula (II-0) or (II), for example, one of $R^1$ and $R^2$ may be H or a protecting group and the other may be H or a phosphate-protecting group. When $R^1$ is the aforementioned protecting group, $R^2$ is preferably H or the aforementioned phosphate-protecting group. When $R^1$ is selected from the aforementioned group I, $R^2$ is preferably H or selected from the aforementioned phosphate-protecting group represented by chemical formula (P3), more preferably H or selected from the aforementioned group II. When $R^1$ is the aforementioned phosphate-protecting group, $R^2$ is preferably H or the aforementioned protecting group. When $R^1$ is a phosphate-protecting group represented by the aforementioned chemical formula (P3) or selected from the aforementioned group II, $R^2$ is preferably H or selected from the aforementioned group I.

Examples of the structure of the aforementioned chemical formula (II-0) or (II) include the following chemical formulas (II-1)-(II-6). In the following chemical formulas (II-1)-(II-6), n and m are the same as in the aforementioned chemical formula (II-0) or (II).

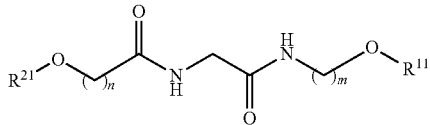

(II-1)

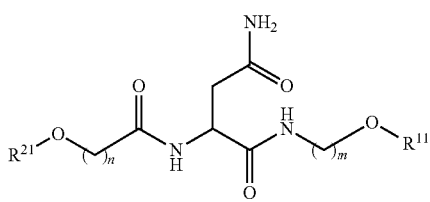

(II-2)

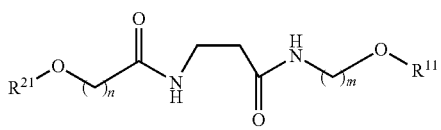

(II-3)

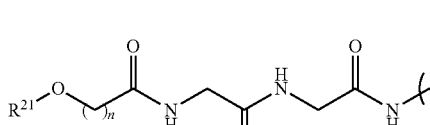

(II-4)

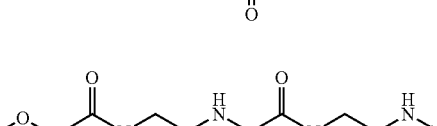

(II-5)

(II-6)

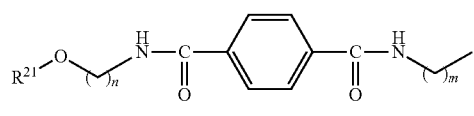

In the aforementioned chemical formulae (II-1) to (II-6), n and m are not particularly limited, and are as described above. Specific examples thereof include n=11 and m=12 in the aforementioned chemical formula (II-1), n=5 and m=4 in the aforementioned chemical formula (II-1), and n=4 and m=4 in the aforementioned chemical formula (II-6). The structures are shown by the following chemical formulas (II-1a), (II-4-a) and (II-6a).

(II-1a)

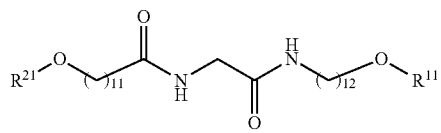

(II-4a)

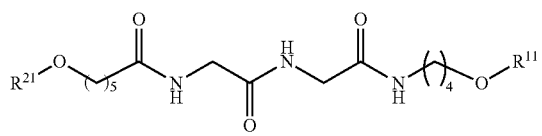

(II-6a)

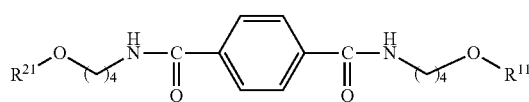

While the production method of a monomer in the present invention is not particularly limited, for example, as shown in the following scheme 1, the following compound (Ic) may be produced from compound (Ib), wherein the amino group of the aforementioned amino acid (Ia) is protected by a protecting group $R^{31}$, by a condensation reaction, (IIa) is produced from (Ic), and (IIa) is converted to (II). The following scheme 1 is an example and the present invention is not limited thereto. In the following chemical formulae (Ib) and (Ic), the protecting group $R^{31}$ is, for example, Fmoc (9-fluorenylmethyloxycarbonyl group), Z (benzyloxycarbonyl), BOC (t-butoxycarbonyl) and the like. In the following chemical formulae (Ib), (Ic) and (IIa), $Y^1$, $Y^2$, L, $L^2$, $R^1$ and $R^{21}$ are as defined for the aforementioned chemical formula (II). The following compound (IIa) is a compound of the aforementioned chemical formula (II) wherein $X^1$ is O and $X^2$ is O. Carbonyl oxygen in the following chemical formula (IIa) may be appropriately converted to $X^1$ and $X^2$ in the aforementioned chemical formula (II). When conversion is not necessary, the following compound (IIa) may be directly used as compound (II). While the production method of the monomer represented by the aforementioned chemical formula (II-0) of the present invention is not particularly limited, for example, it may be the production method of the following scheme 1 or a production method according to the following scheme 1. Specifically, for example, the monomer represented by the aforementioned chemical formula (II-0) of the present invention can also be produced by a production method similar to that in the following scheme 1 except that polyamine or polycarboxylic acid and the like are used instead of the amino acid of the following chemical formula (Ib).

scheme 1

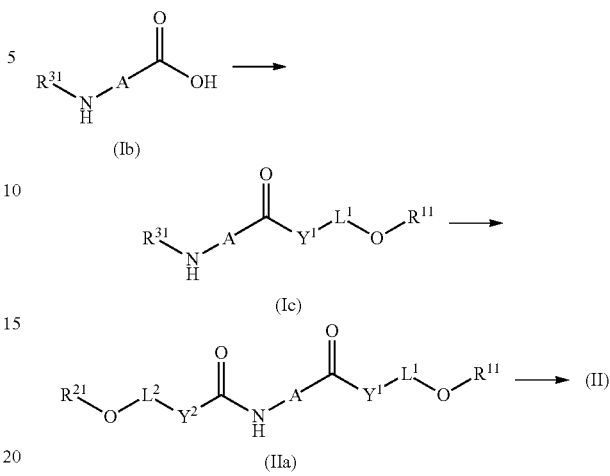

The monomer and the production method thereof in the present invention are further specifically exemplified by the following schemes 2 and 2a. However, the following schemes 2 and 2a are examples, and the present invention is not limited thereto. In the following schemes 2 and 2a, "Fmoc" is a 9-fluorenylmethyloxycarbonyl group, "iPr" is an isopropyl group, "Tr" is a trityl group or triphenylmethyl group, and "ODMTr" is a 4,4'-dimethoxytrityloxy group. Hereinafter the same.

scheme 2

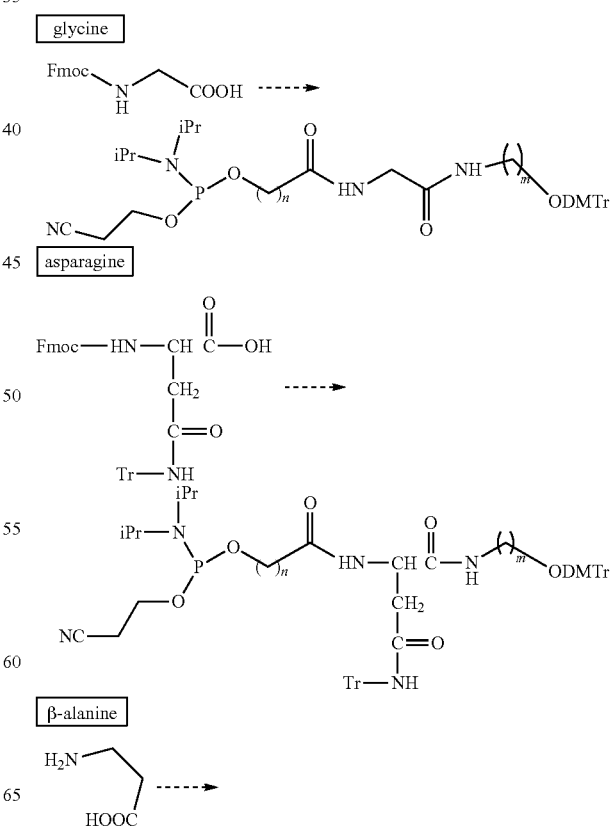

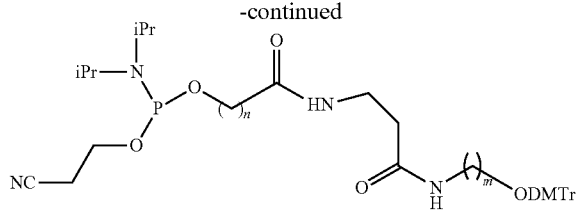
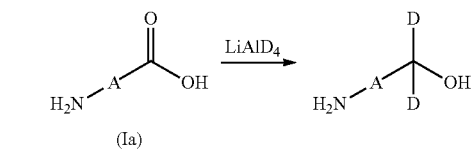

scheme 3

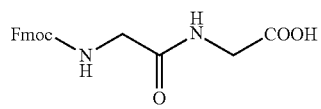

scheme 2a

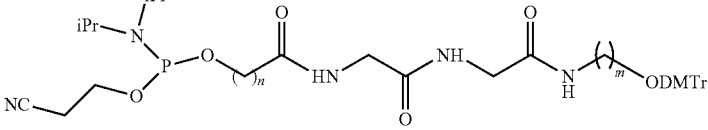

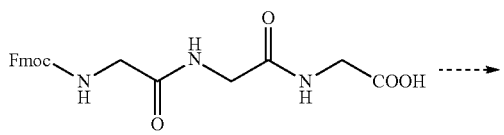

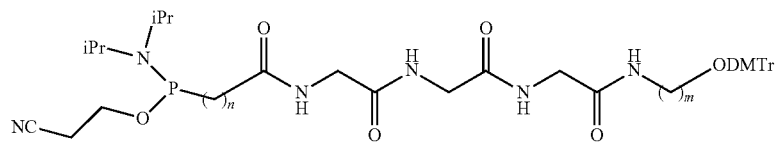

The monomer of the present invention preferably includes, for example, the labeling substance. It is particularly preferable that the monomer of the present invention includes the stable isotope.

When the monomer of the present invention includes an isotope such as the aforementioned stable isotope, the aforementioned isotope can be easily introduced into the microRNA inhibitor molecule of the present invention. The aforementioned monomer including an isotope can be synthesized from, for example, a raw material of amino acid (Ia) into which the aforementioned isotope is introduced. In the present invention, a method of obtaining the amino acid (Ia) into which an isotope is introduced is not particularly limited. For example, it may be produced by an appropriate method, or a commercially available product may be used.

As an amino acid into which the aforementioned stable isotope is introduced, for example, an amino acid into which a heavy hydrogen (D) is introduced can be produced by treating amino acid (Ia) with LiAlD$_4$, as shown in the following scheme 3, and further oxidizing the OH group.

As an amino acid into which other stable isotope is introduced, for example, an amino acid into which a heavy oxygen ($^{18}$O) is introduced can be produced by reacting methyl ester of amino acid (Ia) with H$_2{}^{18}$O under a basic condition, as shown in the following scheme 4.

scheme 4

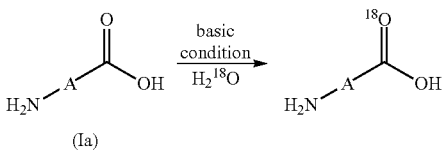

As a peptide introduced with a stable isotope, for example, a peptide introduced with deuterium (D) can be produced by, for example, treating a peptide bond with LiAlD$_4$ as shown in the following scheme 3a.

scheme 3a

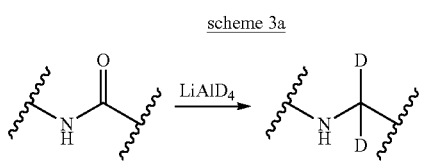

As a peptide introduced with a stable isotope, for example, a peptide introduced with heavy oxygen ($^{18}O$) can be produced by, for example, as shown in the following scheme 4a, under basic condition, reacting carboxylic acid methyl ester with $H_2{}^{18}O$, and thereafter, condensing carboxylic acid in the following chemical formula with an amino group or imino group to form a peptide bond.

scheme 4a

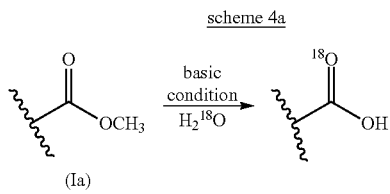

(Ia)

In addition, the production method of the amino acid or peptide including introduction of heavy nitrogen ($^{15}N$) or heavy carbon ($^{13}C$) and the like is not particularly limited, and it can be produced by an appropriate method.

A monomer having a stable isotope introduced thereto can be synthesized in the above-described manner. By using the aforementioned monomer as amidite for synthesis, the microRNA inhibitor of the present invention in which a stable isotope is introduced to the aforementioned amino acid residue can be synthesized. The structure of the terminal portion of the microRNA inhibitor of the present invention may be a nucleic acid. However, a linker residue is preferable, and an amino acid residue (amino acid or peptide) is more preferable.

While the use of the monomer of the present invention is not particularly limited, it is preferably an automatic nucleic acid synthesis. Alternatively, the monomer of the present invention is preferably used for the production of a nucleic acid molecule, and the aforementioned nucleic acid molecule is more preferably the aforementioned microRNA inhibitor of the present invention.

EXAMPLES

The present invention is explained in detail in the following by referring to Examples and the like, which are not to be construed as limitative.

[Synthesis of Molecule for Glycine Residue [Gly] Introduction]

In the oligonucleotides (microRNA inhibitors) of each of the below-mentioned Examples and Reference Examples, the molecule for glycine residue (Gly) introduction (the monomer of the present invention) was synthesized as follows.

That is, in accordance with the following scheme 5, dodecanamidoglycine-4,4'-dimethoxytrityloxydodecanamido phosphoramidite (6) was synthesized. Compound (6) is a molecule for glycine residue (Gly) introduction, and is one embodiment of the aforementioned monomer of the present invention. In the following scheme 5, "Gly" is a structure represented by the following chemical formula, namely, an atom group having a structure wherein one hydrogen atom of amino group and OH of carboxy group have been removed from glycine. In the following, unless otherwise specified, "Gly" shows the structure of the following chemical formula. In the following scheme 5, the NH side of Gly is bound to Fmoc or carbonyl carbon, and the carbonyl carbon (CO) side of Gly is bound to OH or N atom.

(Gly)

—HN—CH$_2$—CO—

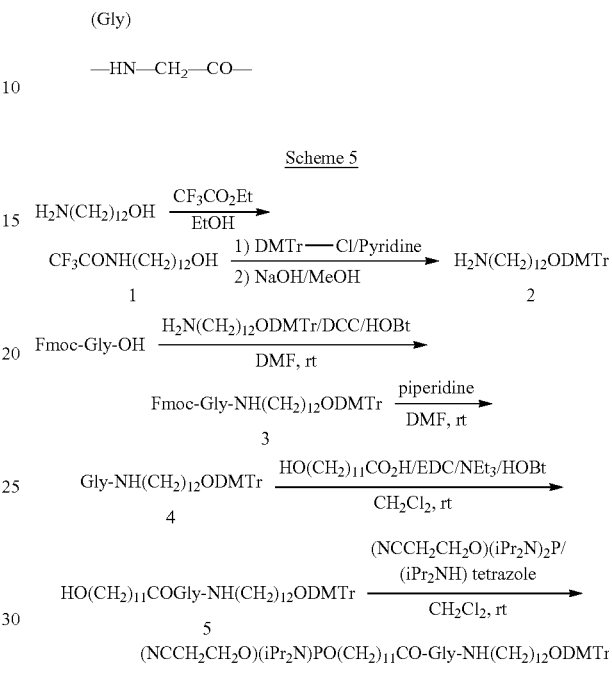

(1) 12-trifluoroacetamidododecanol (Compound 1)

An ethanol solution (100 ml) of 12-aminododecanol (4.81 g, 23.9 mmol) and trifluoroacetic acid ethyl ester (6.79 g, 47.8 mmol) was stirred at room temperature overnight. The reaction mixture was concentrated under reduced pressure to give 12-trifluoroacetamidododecanol (1) (6.98 g, q.) as a colorless syrup.

(2) 12-(4,4'-dimethoxytrityloxy)dodecanamine (Compound 2)

Compound 1 (3.00 g, 10.08 mmol) was dried three times by azeotropic distillation with anhydrous pyridine. To the azeotropic distillation residue were added 4,4'-dimethoxytrityl chloride (4.32 g, 12.1 mmol) and anhydrous pyridine (50 ml), and the mixture was stirred at room temperature overnight. To the obtained reaction mixture was added methanol (10 ml) and the mixture was stirred at room temperature for 30 min. The solvent was evaporated under reduced pressure at room temperature until the mixture became about 30 mL. Thereafter, dichloromethane (200 ml) was added, and the mixture was washed three times with saturated aqueous sodium hydrogen carbonate, and further washed with saturated brine. The mixture was dried over sodium sulfate, and the solvent was evaporated under reduced pressure. To a solution (100 ml) of the thus-obtained unpurified residue in methanol was added sodium hydroxide (2.02 g, 50.40 mmol) and the mixture was stirred at room temperature overnight. The reaction mixture was concentrated under reduced pressure until it became about 30 mL. Water (100 ml) and dichloromethane (200 ml) were added, and the organic layer was fractionated.

The fractionated organic layer was washed with saturated brine, and dried over sodium sulfate. Then, the desiccant (sodium sulfate) was filtered off and the solvent was evaporated under reduced pressure. The obtained residue was purified by silica gel column chromatography (eluent: dichloromethane-methanol (95:5)+0.05% pyridine) to give 12-(4,4'-dimethoxytrityloxy)dodecanamine (2) (5.19 g, q.). The instrumental analysis values of 12-(4,4'-dimethoxytrityloxy)dodecanamine (2) are shown below.

12-(4,4'-dimethoxytrityloxy)dodecanamine (2)

$^1$H-NMR (CDCl$_3$): δ=7.45-7.43 (2H, m), 7.34-7.25 (6H, m), 7.21-7.20 (1H, m), 6.83-6.79 (4H, m), 3.78 (6H, s), 3.04-3.01 (2H, t, J=6.3 Hz), 2.70-2.67 (2H, t, J=6.8 Hz), 1.61-1.54 (6H, m), 1.33-1.24 (14H, m).

(3) Fmoc-glycine-4,4'-dimethoxytrityloxydodecanamide (compound 3)

To a solution (70 ml) of Fmoc-glycine (Fmoc-Gly-OH, purchased from Wako Pure Chemical Industries, Ltd.) (2.00 g, 6.73 mmol), dicyclohexylcarbodiimide (1.66 g, 8.07 mmol) and 1-hydroxybenzotriazole monohydrate (2.31 g, 16.14 mmol) in anhydrous N,N-dimethylformamide was added a solution (30 ml) of compound 2 (4.07 g, 8.07 mmol) in anhydrous N,N-dimethylformamide under an argon atmosphere at room temperature, and the mixture was stirred under an argon atmosphere at room temperature overnight. The resulting precipitate was filtered off, and the filtrate was concentrated under reduced pressure at 35° C. To the obtained residue was added dichloromethane (200 ml), and the mixture was washed 3 times with saturated aqueous sodium hydrogen carbonate. The organic layer was fractionated, dried over sodium sulfate, and the solvent was evaporated under reduced pressure. The obtained residue was purified by silica gel column chromatography (eluent: dichloromethane-methanol (95:5)+0.05% pyridine) to give Fmoc-glycylglycine-4,4'-dimethoxytrityloxybutyldodecanamide (3) (5.88 g, q.) as a colorless syrup.

(4) glycine-4,4'-dimethoxytrityloxydodecanamide (Compound 4)

To compound 3 (5.88 g, 6.73 mmol) were added N,N-dimethylformamide (10 ml) and piperidine (4.8 mL) at room temperature, and the mixture was stirred at room temperature overnight. The solvent was evaporated under reduced pressure and the obtained residue was subjected to silica gel column chromatography (eluent: dichloromethane-methanol (9:1)+0.05% pyridine) to give glycine-4,4'-dimethoxytrityloxydodecanamide (4) (3.44 g, 91%). The instrumental analysis values of glycine-4,4'-dimethoxytrityloxydodecanamide (4) are shown below.

glycine-4,4'-dimethoxytrityloxydodecanamide (4)

$^1$H-NMR (CDCl$_3$): δ=7.47-7.44 (2H, m), 7.33-7.26 (6H, m), 7.21-7.20 (1H, m), 6.83-6.80 (4H, m), 3.79 (6H, s), 3.34 (2H, s), 3.30-3.25 (2H, t, J=6.6 Hz), 3.06-3.02 (2H, t, J=6.3 Hz), 1.64-1.50 (6H, m), 1.38-1.25 (14H, m).

(5) hydroxydodecanamidoglycine-4,4'-dimethoxytrityloxydodecanamide (Compound 5)

Compound 4 (3.15 g, 5.62 mmol) was dried three times by azeotropic distillation with anhydrous pyridine, 12-hydroxydodecanoic acid (3.41 g, 6.74 mmol), 1-ethyl-3-(3-dimethylaminopropyl)carbodiimide hydrochloride (1.29 g, 6.74 mmol), 1-hydroxybenzotriazole monohydrate (2.06 g, 13.48 mmol) and anhydrous dichloromethane (50 ml) were added at room temperature under an argon atmosphere, and the mixture was stirred for 10 min. To the thus-obtained mixture was added triethylamine (2.05 g, 20.22 mmol), and the mixture was stirred at room temperature overnight under an argon atmosphere. To the obtained reaction mixture was added dichloromethane (200 ml), and the mixture was washed three times with saturated aqueous sodium hydrogen carbonate, and further washed once with saturated brine. The organic layer was fractionated, dried over sodium sulfate, and the solvent was evaporated under reduced pressure. The obtained residue was purified by silica gel column chromatography (eluent: dichloromethane-methanol (95:5)+0.05% pyridine) to give hydroxydodecanamidoglycine-4,4'-dimethoxytrityloxydodecanamide (5) (2.97 g, 70%) as a colorless syrup. The instrumental analysis values of hydroxydodecanamidoglycine-4,4'-dimethoxytrityloxydodecanamide (5) are shown below.

hydroxydodecanamidoglycine-4,4'-dimethoxytrityloxydodecanamide (5)

$^1$H-NMR (CDCl$_3$): δ=7.42-7.40 (2H, m), 7.33-7.26 (6H, m), 7.22-7.21 (1H, m), 6.83-6.80 (4H, m), 3.84 (2H, s), 3.79 (6H, s), 3.64-3.61 (2H, t, J=6.3 Hz), 3.26-3.24 (2H, t, J=6.1 Hz), 3.08-3.06 (2H, t, J=5.6 Hz), 2.28-2.24 (2H, t, J=6.8 Hz), 1.69-1.52 (12H, m), 1.44-1.39 (26H, m).

(6) dodecanamidoglycine-4,4'-dimethoxytrityloxydodecanamido phosphoramidite (Compound 6)

Compound 5 (2.78 g, 3.76 mmol) was dried three times by azeotropic distillation with anhydrous pyridine. Then, diisopropylammonium tetrazolide (772 mg, 4.51 mmol) was added, the mixture was deaerated under reduced pressure, filled with argon gas, and anhydrous acetonitrile (3 mL) was added. Furthermore, a solution (3 mL) of 2-cyanoethoxy-N,N,N',N'-tetraisopropyl phosphordiamidite (1.36 g, 4.51 mmol) in anhydrous acetonitrile dichloromethane was added, and the mixture was stirred at room temperature for 4 hr under an argon atmosphere. To the obtained reaction mixture was added dichloromethane (150 ml), and the mixture was washed twice with saturated aqueous sodium hydrogen carbonate, and further washed once with saturated brine. The organic layer was fractionated, dried over sodium sulfate, and the solvent was evaporated under reduced pressure. The residue was subjected to amino silica column chromatography (eluent: n-hexane-acetone(7:3)+0.05% pyridine) to give dodecanamidoglycine-4,4'-dimethoxytrityloxydodecanamido phosphoramidite (6) (2.72 g, 77%, HPLC 98.5%). The instrumental analysis values of dodecanamidoglycine-4,4'-dimethoxytrityloxydodecanamido phosphoramidite (6) are shown below.

dodecanamidoglycine-4,4'-dimethoxytrityloxydodecanamido phosphoramidite (6)

$^1$H-NMR (CDCl$_3$): δ=7.41-7.49 (m, 2H), 7.26-7.30 (m, 6H), 7.17-7.19 (m, 1H), 6.80-6.83 (m, 4H), 6.46-6.62 (m, 2H), 4.07-4.29 (m, 2H), 3.89 (d, J=5.4 Hz, 2H), 3.75-3.87 (m, 4H), 3.67 (s, 6H), 3.47-3.70 (m, 4H), 3.20-3.26 (m, 2H), 3.02 (t, J=6.4 Hz, 2H, CH$_2$), 2.63 (t, 6.4 Hz, 2H, CH$_3$), 1.56-1.63 (m, 6H), 1.47-1.51 (m, 2H), 1.24-1.33 (m, 26H), 1.13-1.20 (m, 12H):
P-NMR (CDCl$_3$): δ=146.62.

In the oligonucleotides of respective Examples and respective Reference Examples, "Gly" is actually represented by the following chemical formula (G1). That is, in the structural formula (sequence) of oligonucleotide of each of the following Examples and Reference Examples, the part other than Gly in the following chemical formula (G1) is omitted for simplification. The N atom in the following chemical formula (G1) is bonded to the carbonyl carbon (CO) side of Gly, and carbonyl carbon in the following chemical formula (G1) is bonded to the NH side of Gly. Also, in oligonucleotide of each of the below-mentioned Examples and Reference Examples, when no base is bonded (not described) to the 5' terminus of Gly (i.e., the following (G1)), a hydrogen atom (H) is bonded to the 5' terminus.

(G1)

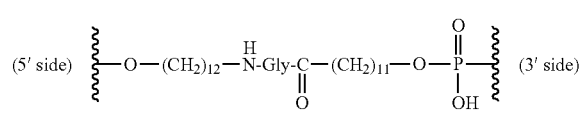

[Synthesis of Molecule for Introduction of Glycine Dimer Residue [GlyGly]]

In the oligonucleotide (microRNA inhibitor) of each of the below-mentioned Examples and Reference Examples, a molecule for introduction of glycine dimer residue (GlyGly) (the monomer of the present invention) was synthesized as follows.

That is, hexanamidoglycylglycine-4,4'-dimethoxytrityloxybutylamido phosphoramidite (16) was synthesized according to the following scheme 6. Compound (16) is a molecule for glycine dimer residue (GlyGly) introduction, and is one example of the aforementioned monomer of the present invention. The "Gly" in the following scheme 6 shows, as mentioned above, a structure represented by the following chemical formula; that is, an atomic group having a structure wherein one hydrogen atom of the amino group and OH of the carboxy group have been removed from glycine. Unless otherwise specified, in the following scheme 6, the "GlyGly" has a structure wherein two Glys are linked to form a peptide bond (below). In the following scheme 6, Fmoc or carbonyl carbon is bonded to the NH side of GlyGly and OH or N atom is bonded to the carbonyl carbon (CO) side of Gly.

(Gly)

—HN—CH$_2$—CO—

(GlyGly)

—HN—CH$_2$—CO—HN—CH$_2$—CO—

Scheme 6

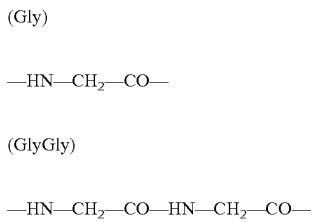

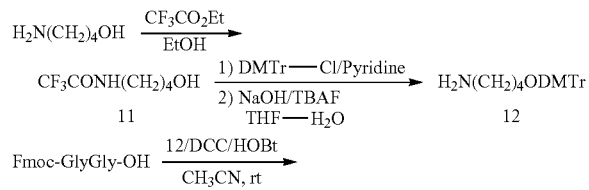

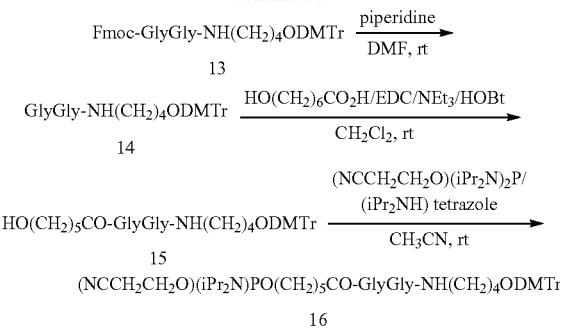

(1) 4-trifluoroacetamidobutanol (Compound 11)

A solution (100 ml) of 4-aminobutanol (2.50 g, 28.05 mmol) and trifluoroacetic acid ethyl ester (19.92 g, 140.26 mmol) in ethanol was stirred at room temperature overnight. The reaction mixture was concentrated under reduced pressure to give 4-trifluoroacetamidobutanol (11) (5.44 g, q.) as a colorless syrup.

(2) 4-(4,4'-dimethoxytrityloxy)butylamine (Compound 12)

Compound 1 (4.15 g, 22.40 mmol) was dried three times by azeotropic distillation with anhydrous pyridine. To the azeotropic distillation residue were added 4,4'-dimethoxytrityl chloride (9.60 g, 28.3 mmol) and anhydrous pyridine (100 ml), and the mixture was stirred at room temperature overnight. To the obtained reaction mixture was added methanol (10 ml), the mixture was stirred at room temperature for 30 min, and the solvent was evaporated under reduced pressure at room temperature to about 20 mL. Thereafter, dichloromethane (200 ml) was added, and the mixture was washed three times with saturated aqueous sodium hydrogen carbonate, and further washed with saturated brine. The mixture was dried over sodium sulfate, and the solvent was evaporated under reduced pressure. To a solution (50 ml) of the thus-obtained unpurified residue (9.00 g) in tetrahydrofuran was added a solution (70 ml) of sodium hydroxide (3.71 g, 92.7 mmol) in water. While vigorously stirring the mixture at room temperature, tetrabutylammonium fluoride trihydrate (180 mg) was added and the mixture was further stirred vigorously at room temperature overnight. To the obtained reaction mixture were added ethyl acetate (200 ml) and water (100 ml), and the organic layer was fractionated. The aqueous layer was further extracted with ethyl acetate, and the extract was combined with the organic layer fractionated in advance, and dried over sodium sulfate. Thereafter, the desiccant (sodium sulfate) was filtered off and the solvent was evaporated under reduced pressure. The obtained residue was subjected to silica gel column chromatography (eluent: dichloromethane-methanol (9:1)+0.05% pyridine) to give 4-(4,4'-dimethoxytrityloxy)butylamine (12) (6.36 g, 87%). The instrumental analysis values of 4-(4,4'-dimethoxytrityloxy)butylamine (12) are shown below.

4-(4,4'-dimethoxytrityloxy)butylamine (2)

$^1$H-NMR (CDCl$_3$): δ=7.42-7.45 (m, 2H), 7.26-7.34 (m, 12H), 7.17-7.20 (m, 1H), 6.80-6.84 (m, 4H), 3.79 (s, 6H), 3.48 (s, 2H, NH$_2$), 3.06 (t, 6.8 Hz, 2H, CH$_2$), 2.67 (t, 7.4 Hz, 2H, CH$_2$), 1.60-1.65 (m, 2H, CH$_2$), 1.49-1.55 (m, 2H, CH$_2$)

(13) Fmoc-glycylglycine-4,4'-dimethoxytrityloxybutylamide (compound 13)

To a solution (70 ml) of Fmoc-glycylglycine (Fmoc-GlyGly-OH, purchased from China Langchem) (2.50 g, 7.05 mmol), dicyclohexylcarbodiimide (1.75 g, 8.46 mmol) and 1-hydroxybenzotriazole monohydrate (2.59 g, 16.92 mmol) in anhydrous N,N-dimethylformamide was added a solution (50 ml) of compound 12 (3.31 g, 8.46 mmol) in anhydrous N,N-dimethylformamide under ice-cooling under an argon atmosphere. After removing the ice bath, the mixture was stirred at room temperature overnight under an argon atmosphere. The resulting precipitate was filtered off, and the filtrate was concentrated at 35° C. under reduced pressure. To the obtained residue was added dichloromethane (200 ml), and the mixture was washed twice with saturated brine. The organic layer was fractionated, dried over sodium sulfate, and the solvent was evaporated under reduced pressure. The residue was purified by silica gel column chromatography (eluent: dichloromethane-methanol (95:5)+0.05% pyridine, and then dichloromethane-methanol (9:1)+0.05% pyridine) to give Fmoc-glycylglycine-4,4'-dimethoxytrityloxybutylamide (13) (3.49 g, 68%) as a colorless syrup.

(14) glycylglycine-4,4'-dimethoxytrityloxybutylamide (compound 14)

To compound 13 (3.00 g, 4.12 mmol) were added acetonitrile (5 mL) and piperidine (2.4 mL) at room temperature, and the mixture was stirred at room temperature overnight. The solvent was evaporated under reduced pressure, and the obtained residue was subjected to silica gel column chromatography (eluent: dichloromethane-methanol (9:1)+0.05% pyridine) to give glycylglycine-4,4'-dimethoxytrityloxybutylamide (14) (1.13 g, 54%). The instrumental analysis values of glycylglycine-4,4'-dimethoxytrityloxybutylamide (14) are shown below.

glycylglycine-4,4'-dimethoxytrityloxybutylamide (14)

$^1$H-NMR (CDCl$_3$): δ=7.40-7.42 (m, 2H), 7.25-7.31 (m, 12H), 7.19-7.21 (m, 1H), 6.80-6.84 (m, 4H), 3.89 (d, J=5.9 Hz, 2H), 3.79 (s, 6H), 3.37 (s, 2H), 3.25 (t, J=5.8 Hz, 2H, CH$_2$), 2.67 (t, J=5.8 Hz, 2H, CH$_2$), 1.57-1.65 (m, 4H, CH$_2$).

(15) hydroxyhexanamidoglycylglycine-4,4'-dimethoxytrityloxybutylamide (Compound 15)

Compound 14 (1.07 g, 2.11 mmol) was dried three times by azeotropic distillation with anhydrous acetonitrile, 6-hydroxyhexanoic acid (336 mg, 2.54 mmol), 1-ethyl-3-(3-dimethylaminopropyl)carbodiimide hydrochloride (487 mg, 2.54 mmol), 1-hydroxybenzotriazole monohydrate (778 mg, 5.08 mmol) and anhydrous dichloromethane (20 ml) were added at room temperature, and the mixture was stirred for 10 min under an argon atmosphere. To the thus-obtained mixture was added triethylamine (778 mg, 5.08 mmol), and the mixture was stirred at room temperature overnight under an argon atmosphere. To the obtained reaction mixture was added dichloromethane (150 ml), and the mixture was washed three times with saturated aqueous sodium hydrogen carbonate, and further washed once with saturated brine. The organic layer was fractionated and dried over sodium sulfate, and the solvent was evaporated under reduced pressure. The obtained residue was purified by silica gel column chromatography (eluent: dichloromethane-methanol (95:5)+0.05% pyridine) to give hydroxyhexanamidoglycylglycine-4,4'-dimethoxytrityloxybutylamide (15) (890 mg, 68%) as a colorless syrup. The instrumental analysis values of hydroxyhexanamidoglycylglycine-4,4'-dimethoxytrityloxybutylamide (15) are shown below.

hydroxyhexanamidoglycylglycine-4,4'-dimethoxytrityloxybutylamide (15)

$^1$H-NMR (CDCl$_3$): δ=7.41-7.42 (m, 2H), 7.27-7.34 (m, 12H), 7.18-7.21 (m, 1H), 6.81-6.83 (m, 4H), 3.92 (d, J=5.43 Hz, 2H, CH$_2$), 3.84 (d, J=5.9 Hz, 2H), 3.79 (s, 6H), 3.60 (m, 2H, CH$_2$), 3.23-3.28 (m, 2H, CH$_2$), 3.05-3.10 (m, 2H, CH$_2$), 2.56 (t, J=7.3 Hz, 2H, CH$_2$), 1.50-1.72 (m, 8H), 1.30-1.45 (m, 2H, CH$_2$).

(16) hexanamidoglycylglycine-4,4'-dimethoxytrityloxybutylamido phosphoramidite (Compound 16)

Compound 15 (824 mg, 1.33 mmol) was dried three times by azeotropic distillation with anhydrous pyridine. Then, diisopropylammonium tetrazolide (274 mg, 1.60 mmol) was added, the mixture was deaerated under reduced pressure, filled with argon gas, and anhydrous acetonitrile (1 mL) was added. Furthermore, a solution (1 ml) of 2-cyanoethoxy-N,N,N',N'-tetraisopropyl phosphordiamidite (482 mg, 1.60 mmol) in anhydrous acetonitrile was added, and the mixture was stirred at room temperature for 4 hr under an argon atmosphere. To the obtained reaction mixture was added dichloromethane (100 ml), and the mixture was washed twice with saturated aqueous sodium hydrogen carbonate, and further washed once with saturated brine. The organic layer was fractionated, dried over sodium sulfate, and the solvent was evaporated under reduced pressure. The residue was subjected to amino silica column chromatography (eluent: dichloromethane-acetone (7:3)+0.05% pyridine) to give hexanamidoglycylglycine-4,4'-dimethoxytrityloxybutylamido phosphoramidite (16) (938 mg, 86%, HPLC 98.2%). The instrumental analysis values of hexanamidoglycylglycine-4,4'-dimethoxytrityloxybutylamido phosphoramidite (16) are shown below.

hexanamidoglycylglycine-4,4'-dimethoxytrityloxybutylamido phosphoramidite (16)

$^1$H-NMR (CDCl$_3$): δ=7.36-7.47 (m, 3H), 7.24-7.30 (m, 5H), 7.18-7.19 (m, 1H), 6.80-6.82 (m, 4H), 3.92 (d, J=4.9 Hz, 2H, CH$_2$), 3.84 (d, J=5.4 Hz, 2H), 3.76 (s, 6H), 3.73-3.85 (m, 4H), 3.54-3.64 (m, 4H), 3.18-3.25 (m, 2H, CH$_2$), 3.05-3.10 (m, 2H, CH$_2$), 2.60 (t, J=6.3 Hz, 2H, CH$_2$), 2.23 (t, 7.4 Hz, 2H, CH$_2$), 1.55-1.68 (m, 8H), 1.30-1.45 (m, 2H, CH$_2$). 1.15-1.18 (m, 12H):

P-NMR (CDCl$_3$): δ=146.57.

HPLC: Retention time 6.25 min (Shimadzu SPD-10AV (XBridge OST C18, 4.6 mM×50 mm))

In each of the following Examples, "GlyGly" in the oligonucleotides of respective Examples and respective Reference Examples is in fact represented by the following chemical formula (G2). That is, in the structural formula (sequence) of oligonucleotide of each of the following Examples and Reference Examples, the part other than GlyGly in the following chemical formula (G2) is omitted for simplification. GlyGly in the following chemical formula (G2) has a structure wherein two Glys mentioned above are linked to form a peptide bond. The N atom in the following chemical formula (G2) is bonded to the carbonyl carbon (CO) side of GlyGly, and carbonyl carbon in the following chemical formula (G2) is bonded to the NH side of GlyGly. Also, in oligonucleotide of each of the below-mentioned Examples and Reference Examples, when no base is bonded (not described) to the 5' terminus of GlyGly (i.e., the following (G2)), a hydrogen atom (H) is bonded to the 5' terminus.

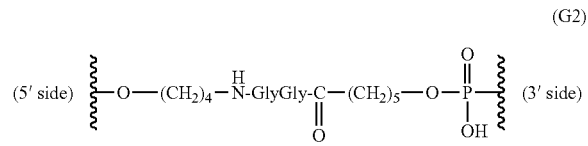

(G2)

[Synthesis of Molecule for Introduction of Terephthalamide Residue [TPA]]

In the oligonucleotide (microRNA inhibitor) of each of the below-mentioned Examples and Reference Examples, a terephthalic acid amidite which is a molecule for introduction of terephthalamide residue (TPA) (the monomer of the present invention) was synthesized according to the following scheme 7. While TPA is described as "terephthalamide residue", it can also be a terephthalic acid residue.

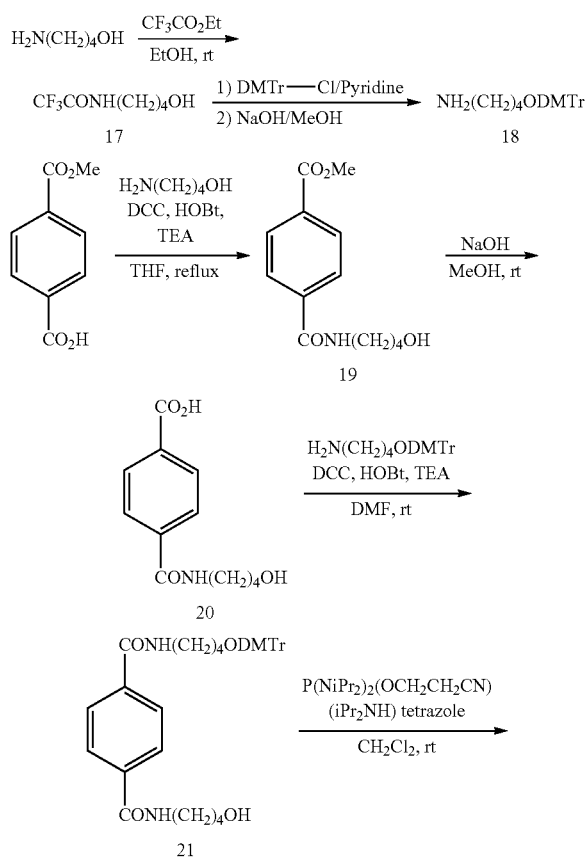

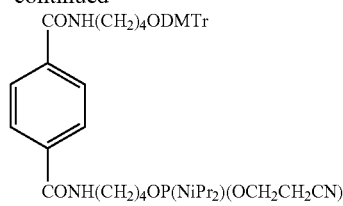

(1) Compound 17

A solution (100 ml) of 4-aminobutanol (2.50 g, 28.05 mmol) and trifluoroacetic acid ethyl ester (19.92 g, 140.22 mmol) in ethanol was stirred at room temperature overnight. The reaction mixture was concentrated under reduced pressure to give compound 17 (5.20 g, q.).

(2) Compound 18

A solution (20 ml) of compound 17 (5.20 g, 28.05 mmol) and 4,4'-dimethoxytrityl chloride (11.40 g, 33.66 mmol) in anhydrous pyridine was stirred at room temperature overnight. Dichloromethane (200 ml) was added, and the mixture was washed three times with saturated aqueous sodium hydrogen carbonate, and further washed with saturated brine. After drying over sodium sulfate, the solvent was evaporated under reduced pressure. To a solution (100 ml) of the thus-obtained unpurified residue in methanol was added sodium hydroxide (5.61 g, 140.23 mmol), and the mixture was stirred at room temperature overnight. The reaction mixture was concentrated under reduced pressure, water (200 ml) was added, and the mixture was extracted twice with dichloromethane (200 ml). The organic layer was fractionated, dried over sodium sulfate, and the solvent was evaporated under reduced pressure. The obtained residue was subjected to silica gel column chromatography (eluent: dichloromethane-methanol (9:1)+0.05% pyridine) to give compound 18 (8.20 g, 75%). The instrumental analysis values of compound 18 are shown below.

Compound 18

$^1$H-NMR (CDCl$_3$): δ=7.44-7.42 (2H, m), 7.34-7.25 (6H, m), 7.20 (1H, d, J=7.3 Hz), 6.82 (4H, m), 3.78 (6H, s), 3.06 (2H, t, J=6.3 Hz), 2.68 (2H, t, J=7.1 Hz), 1.59 (4H, m).

(3) Compound 19

A solution (70 ml) of terephthalic acid monomethyl (3.00 g, 16.65 mmol), 4-aminobutanol (0.89 g, 9.98 mmol), dicyclohexylcarbodiimide (2.06 g, 9.98 mmol), 1-hydroxybenzotriazole monohydrate (3.06 g, 19.96 mmol) and triethylamine (5.05 g, 49.9 mmol) in anhydrous tetrahydrofuran was stirred while refluxing for 5 hr. After cooling to room temperature, the resulting precipitate was filtered off, and the filtrate was concentrated under reduced pressure. To the residue was added ethyl acetate (50 ml), and the precipitate was collected by filtration to give the object compound 19 (1.52 g). The filtrate was concentrated under reduced pressure, and washed with toluene. The precipitate was collected by filtration to give the object compound 19 (0.83 g). To the filtrate was added dichloromethane (200 ml), and the mixture was washed twice with saturated aqueous sodium hydrogen carbonate, and further washed with saturated brine. After drying over sodium sulfate, the solvent was evaporated under reduced pressure to give the object compound 19 (0.37 g). A total of the obtained object products (compound 19) was yield 2.72 g, yield 65%. The instrumental analysis values of compound 19 are shown below.

Compound 19

$^1$H-NMR (CDCl$_3$): δ=8.10-8.07 (2H, m), 7.83 (2H, m), 3.94 (3H, s), 3.74 (2H, t, J=5.9 Hz), 3.50 (2H, m), 1.92 (2H, dd, J=12.7, 3.4 Hz), 1.80-1.65 (2H, m).

(4) Compound 20

A solution (70 ml) of compound 19 (2.33 g, 9.27 mmol) and sodium hydroxide (1.85 g, 46.36 mmol) in methanol was stirred at room temperature overnight. The reaction mixture was concentrated under reduced pressure, and water was added. Furthermore, the mixture was adjusted with 2N (2 mol/L) hydrochloric acid to pH 2. The resulting precipitate was collected by filtration and dried under reduced pressure to give the object compound 20 (1.95 g, 89%). The instrumental analysis values of compound 20 are shown below.

Compound 20

$^1$H-NMR (DMSO-d$_6$): δ=8.00 (2H, d, J=8.3 Hz), 7.92 (2H, d, J=8.3 Hz), 1.72 (2H, d, J=12.7 Hz), 1.63-1.45 (4H, m), 1.15 (2H, m).

(5) Compound 21

A solution (170 ml) of compound 18 (3.09 g, 7.88 mmol), compound 20 (1.70 g, 7.16 mmol), dicyclohexylcarbodiimide (1.63 g, 7.88 mmol), 1-hydroxybenzotriazole monohydrate (2.41 g, 15.76 mmol) and triethylamine (3.62 g, 35.80 mmol) in anhydrous N,N-dimethylformamide was stirred at room temperature overnight under an argon atmosphere. The obtained reaction mixture was concentrated under reduced pressure, dichloromethane (300 ml) was added, and the mixture was washed 3 times with saturated aqueous sodium hydrogen carbonate. The organic layer was fractionated, dried over sodium sulfate, and the solvent was evaporated under reduced pressure. The residue was triturated with toluene, the resulting precipitate was collected by filtration and dried under reduced pressure to give the object compound 21 (3.94 g, 90%). The instrumental analysis values of compound 21 are shown below.

Compound 21

$^1$H-NMR (CDCl$_3$): δ=7.76-7.67 (4H, m), 7.40 (2H, d, J=7.3 Hz), 7.27 (6H, m), 7.19 (1H, m), 6.80 (4H, d, J=8.8 Hz), 3.78 (6H, s), 3.73 (2H, t, J=5.9 Hz), 3.48 (4H, m), 3.12 (2H, t, J=5.6 Hz), 1.72 (8H, m).

(6) Compound 22

Compound 21 (1.50 g, 2.46 mmol) was dried three times by azeotropic distillation with anhydrous pyridine. Then, diisopropylammonium tetrazolide (630 mg, 3.68 mmol) was added, the mixture was deaerated under reduced pressure, filled with argon gas, and anhydrous dichloromethane (1 mL) was added. Furthermore, a solution (1 ml) of 2-cyanoethoxy-N,N,N',N'-tetraisopropyl phosphordiamidite (1.11 g, 3.68 mmol) in anhydrous dichloromethane was added, and the mixture was stirred at room temperature for 4 hr under an argon atmosphere. To the obtained reaction mixture was added dichloromethane (200 ml), and the mixture was washed 3 times with saturated aqueous sodium hydrogen carbonate. The organic layer was fractionated, dried over sodium sulfate, and the solvent was evaporated under reduced pressure. The residue was dissolved with dichloromethane, and subjected to amino silica column chromatography (eluent: n-hexane-acetone (7:3)+0.05% pyridine) to give compound 22 (1.86 g, 93%). The instrumental analysis values of compound 22 are shown below.

Compound 22

$^1$H-NMR (CDCl$_3$): δ=7.74 (4H, m), 7.41 (2H, m), 7.31-7.24 (6H, m), 7.20 (1H, m), 6.80 (4H, m), 3.85-3.56 (10H, m), 3.45 (4H, m), 3.12 (2H, t, J=5.9 Hz), 2.60 (2H, dd, J=11.0, 4.6 Hz), 2.16 (2H, t, J=3.4 Hz), 1.72 (8H, t, J=5.9 Hz), 1.17 (12H, m). $^{31}$P-NMR (CDCl$_3$): δ=147.10.

The "TPA" in the oligonucleotides of respective Examples and respective Reference Examples to be mentioned below actually has a structure represented by the following chemical formula. Also, in oligonucleotide of each of the below-mentioned Examples and Reference Examples, when no base is bonded (not described) to the 5' terminus of TPA, a hydrogen atom (H) is bonded to the 5' terminus.

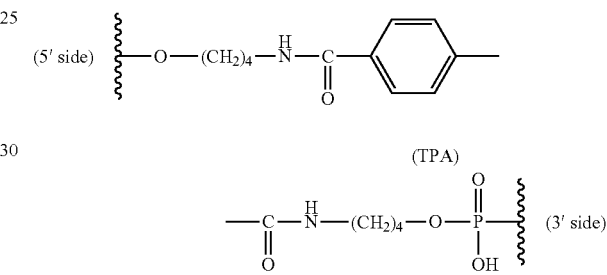

(TPA)

Example 1

Figure 4:
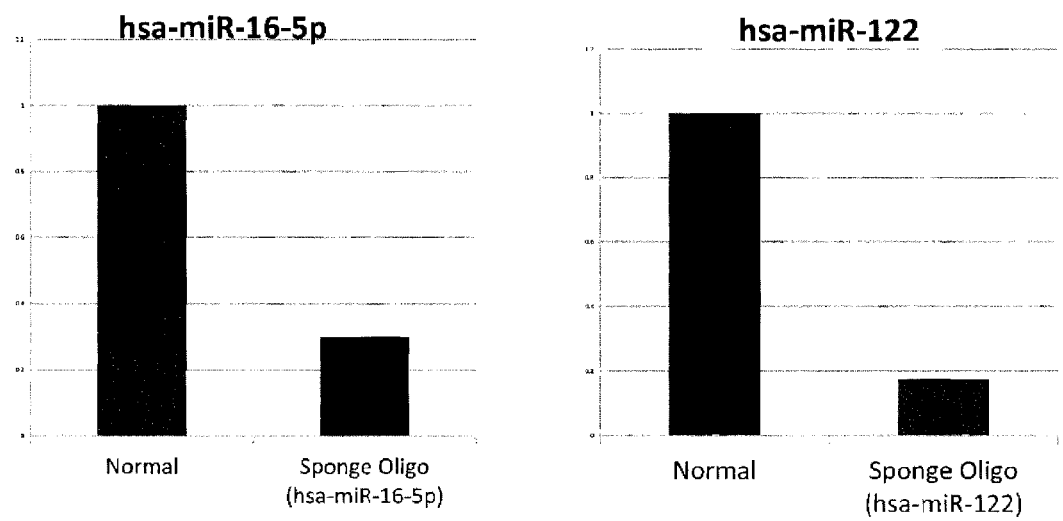
FIG. 4 shows the results of confirmation of the expression level of the microRNA of Example 1 by qPCR.

Using two microRNAs of hsa-miR-16-5p and hsa-miR-122 as the inhibition target, microRNA inhibitors were produced by the aforementioned chemical synthesis method as shown below. First, the aforementioned complementary sequences were complementary to the whole or a part of the sequences of the aforementioned two microRNAs. Three of the aforementioned complementary sequences were linked by a glycine residue (Gly), and the glycine residue (Gly) was also linked to each terminal portion of the aforementioned complementary sequences present at both ends. The aforementioned two kinds of microRNA inhibitors were introduced into Huh-7 cells, and the expression level of microRNA recovered 24 hr after the introduction was confirmed by qPCR. The results are shown in FIG. 4. As shown in the Figure, it is clear that the two microRNA inhibitors (Sponge Oligo) of this example dominantly inhibited microRNAs as compared to when they were not introduced (Normal).

In Example 1 and each of the below-mentioned Examples (including Reference Examples), the microRNA inhibitor was synthesized from the 3' side to the 5' side by a nucleic acid synthesizer (trade name ABI Expedite (registered trade mark) 8909 Nucleic Acid Synthesis System, applied biosystems) based on the phosphoramidite method. In the aforementioned synthesis, RNA Phosphoramidites (2'-O-TBDMSi, trade name, Samchully Pharm Co., Ltd.) was used as RNA amidite. As DNA amidite, DNA Phosphoramidites (Samchully Pharm Co., Ltd.) were used. In addition, a molecule for glycine residue (Gly) introduction and a molecule for glycine dimer residue (GlyGly) introduction to be used for the aforementioned phosphoramidite method were synthesized by the below-mentioned method. These molecule for glycine residue (Gly) introduction and glycine dimer residue (GlyGly) introduction were amidites, which correspond to the aforementioned monomer of the present invention. The deprotection of the aforementioned amidite followed a conventional method, and the synthesized microRNA inhibitors were purified by HPLC.

Example 2

Comparison of Suppressive Effect of Sponge Oligonucleotide (Example) and Monomer Decoy Oligonucleotide (Reference Example) on hsa-miR-16-5p (miR-16) Activity in HCT116 Cells (1) Material
1-a: Oligonucleotide As shown in the below-mentioned base sequences and Table 1 below, microRNA inhibitors wherein sequences complementary to the sequence of hsa-miR-16-5p (microRNA) were linked by Gly (the aforementioned G1) or GlyGly (the aforementioned G2) were used to measure their microRNA suppressive effect (microRNA inhibitory activity). In the following, hsa-miR-16-5p is simply referred to as "miR-16". In the present Example and the below-mentioned respective Examples (including Reference Examples), microRNA is miR-16, unless otherwise specified.

In the present Example (Example 2) and each of the following Examples, a microRNA inhibitor having two or more sequences complementary to the sequence of microRNA is referred to as "sponge oligonucleotide" or "sponge oligo". A microRNA inhibitor (Reference Example) having only one sequence complementary to the sequence of microRNA is referred to as "monomer decoy oligonucleotide" or "monomer decoy". Moreover, in the present Example (Example 2) and each of the below-mentioned Examples, "Perfect type" means a microRNA inhibitor having a full match structure of FIG. 3(a), the "Bulge type" refers to a microRNA inhibitor having a mismatch structure of FIG. 3(b), and the "Bubble type" refers to a microRNA inhibitor having a mismatch structure of FIG. 3(c).

(Example 2-1)
spo-D-3(Gly-containing Bubble type sponge oligo)
(SEQ ID NO: 2)
5'-Gly-CGCCAATATTCGATGCTGCTA-Gly-CGCCAATATTCGATGCT
GCTA-Gly-CGCCAATATTCGATGCTGCTA-Gly-T-3'

(Reference Example 2-1)
spo-D-7(Gly-containing Bubble type monomer decoy)
(SEQ ID NO: 3)
5'-Gly-CGCCAATATTCGATGCTGCTA-Gly-T-3'

(Example 2-2)
spo-D-13(GlyGly-containing Perfect type sponge oligo)
(SEQ ID NO: 4)
5'-GlyGly-CGCCAATATTTACGTGCTGCTA-GlyGly-CGCCAATATT
TACGTGCTGCTA-GlyGly-CGCCAATATTTACGTGCTGCTA-
GlyGly-T-3'

(Reference Example 2-2)
spo-D-14(GlyGly-containing Perfect type monomer decoy)
(SEQ ID NO: 5)
5'-GlyGly-CGCCAATATTTACGTGCTGCTA-GlyGly-T-3'

(Example 2-3)
spo-D-16(GlyGly-containing Bubble type sponge oligo)
(SEQ ID NO: 6)
5'-GlyGly-CGCCAATATTCGATGCTGCTA-GlyGly-CGCCAATATTC
GATGCTGCTA-GlyGly-CGCCAATATTCGATGCTGCTA-
GlyGly-T-3'

(Reference Example 2-3)
spo-D-17(GlyGly-containing Bubble type monomer decoy)
(SEQ ID NO: 7)
5'-GlyGly-CGCCAATATTCGATGCTGCTA-GlyGly-T-3'

As a negative control for each of the above-mentioned Examples 2-1-2-3, the following Reference Examples 2-4-2-6 were used.

(Reference Example 2-4)
spo-D-9 (Gly-containing Bubble type sponge oligo negative control)
(SEQ ID NO: 8)
5'-Gly-CGCCAATATTCCATTATAAGA-Gly-CGCCAATATTCCATTAT
AAGA-Gly-CGCCAATATTCCATTATAAGA-Gly-T-3'

(Reference Example 2-5)
spo-D-18 (GlyGly-containing Perfect type sponge oligo negative control)
(SEQ ID NO: 9)
5'-GlyGly-CGCCAATATTTACGTAATTACA-GlyGly-CGCCAATATT
TACGTAATTACA-GlyGly-CGCCAATATTTACGTAATTACA-
GlyGly-T-3'

(Reference Example 2-6)
spo-D-20 (GlyGly-containing Bubble type sponge oligo negative control)
(SEQ ID NO: 10)
5'-GlyGly-CGCCAATATTCCATTATAAGA-GlyGly-CGCCAATATTC
CATTATAAGA-GlyGly-CGCCAATATTCCATTATAAGA-
GlyGly-T-3'

Furthermore, as the microRNA inhibitors of the following Reference Examples 2-7 and 2-8, the positive control (LNA-miR16) of the suppressive effect on miR-16 activity, and the following LNA molecule (manufactured by EXIQON) which is a negative control thereof (LNA-Neg.Con) were used.

(Reference Example 2-7)
hsa-miR-16 miRCURY LNA microRNA Power Inhibitor (426845-00) (LNA-miR16)
(SEQ ID NO: 11)
GCCAATATTTACGTGCTGCT (Reference Example 2-8)
miRCURY LNATM microRNA Power Antisense Control B (199021-00) (LNA-Neg.Con)
(SEQ ID NO: 12)
AGAGCTCCCTTCAATCCAAA The above-mentioned aqueous oligonucleotide solutions were prepared with distilled water for injection to a concentration of 10 μM.

TABLE 1

| Example 2-1 | spo-D-3 (D-3 G-sponge) | Gly-containing Bubble type sponge oligo |
|---|---|---|
| Example 2-2 | spo-D-13 (D-13 GG-sponge) | GlyGly-containing Perfect type sponge oligo |
| Example 2-3 | spo-D-16 (D-16 GG-sponge) | GlyGly-containing Bubble type sponge oligo |
| Reference Example 2-1 | spo-D-7 (D-7 G-monomer) | Gly-containing Bubble type monomer decoy |
| Reference Example 2-2 | spo-D-14 (D-14 GG-monomer) | GlyGly-containing Perfect type monomer decoy |
| Reference Example 2-3 | spo-D-17 (D-17 GG-monomer) | GlyGly-containing Bubble type monomer decoy |
| Reference Example 2-4 | spo-D-9 (D-9 G-Neg. Con) | Gly-containing Bubble type sponge oligo Neg. Con |
| Reference Example 2-5 | spo-D-18 (D-18 GG-Neg. Con) | GlyGly-containing Perfect type sponge oligo Neg. Con |
| Reference Example 2-6 | spo-D-20 (D-20 GG-Neg. Con) | GlyGly-containing Bubble type sponge oligo Neg. Con |

TABLE 1-continued

| | |
|---|---|
| Reference Example 2-7 | LNA-miR16 |
| Reference Example 2-8 | LNA-Neg. Con |

1-b: Cell Line and Medium

The cell line used was human colon cancer cell line HCT116 (ATCC). As the medium, DMEM medium containing 10% FBS (Nacalai) was used for culture at 37° C. in the presence of 10% $CO_2$.

1-c: Reporter Plasmid

As the reporter plasmid, a plasmid containing the following reporter gene was used.

(1) pGL4-miR16

Figure 5:
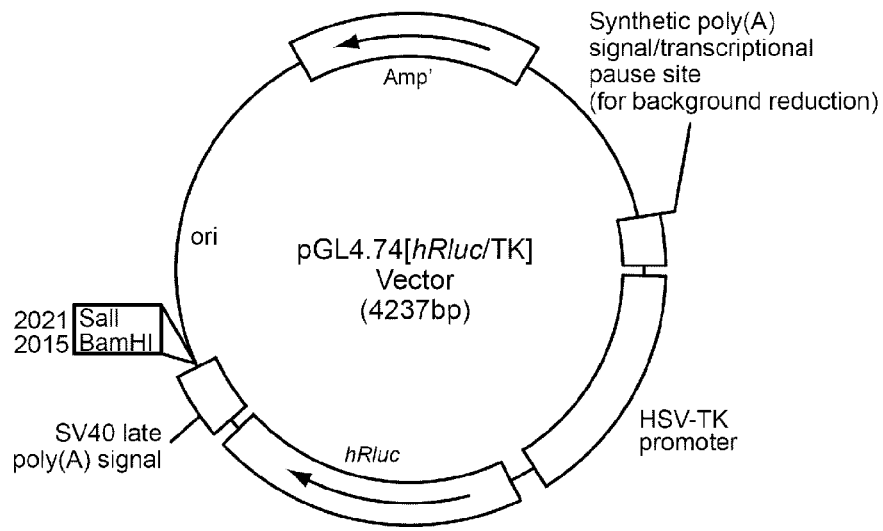
FIG. 5 is a schematic showing of the expression of Renilla luciferase gene by the plasmid used in the Examples.

The pGL4.74[hRluc/TK] vector of Promega KK is, as shown in FIG. 5, a plasmid that expresses Renilla luciferase gene under the control of HSV-TK promoter. pGL4-miR16 is a plasmid incorporating a target sequence of miR-16 at the downstream of the luciferase gene in this vector, which has a structure for suppressing the expression level of luciferase by the activity of miR-16.

(2) pGL4-NTC pGL4-NTC is a plasmid incorporating a non-specific sequence that does not react with miR-16 at the downstream of luciferase gene in the aforementioned pGL4.74[hRluc/TK] vector, and used as a control for pGL4-miR16.

Figure 6:
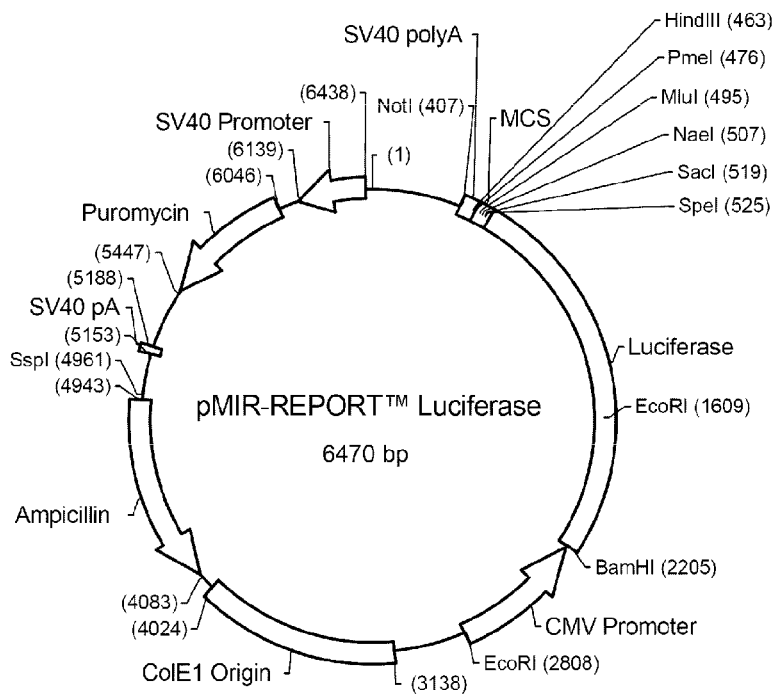
FIG. 6 is a schematic showing of the expression of firefly luciferase gene by a different plasmid used in the Examples.

(3) pMIR-REPORT Luciferase pMIR-REPORT Luciferase of Ambion is, as shown in FIG. 6, a plasmid that expresses firefly luciferase gene under the control of CMV promoter. It was used to monitor the transfection efficiency by cotransfection with the aforementioned pGL4-miR16 or the aforementioned GL4-NTC.

(2) Method 2-a: Transfection of Reporter Gene to HCT116 Cells

The aforementioned HCT116 cells were plated on a 6 cm dish at a density of $1 \times 10^5/cm^2$, and cultured in DMEM medium (10% FBS) free of antibiotics. In addition, OptiMEM (Gibco, 500 µl) added with pGL4-NTC (2 µg) and pMIR-REPORT (2 µg), or OptiMEM added with pGL4-miR16 (2 µg) and pMIR-REPORT (2 µg) was prepared (solution A). Also, Lipofectamine 2000 (Invitrogen, 20 µL) was added to OptiMEM (500 µL) in a different tube (solution B). The both solutions were stirred well, stood at room temperature for 5 min, solution A and solution B were mixed, and stood at room temperature for 20 min, during which time the medium of the aforementioned plated cells was exchanged with a fresh medium. After 20 min, the mixture of the aforementioned solution A and solution B was added to the aforementioned culture medium containing the cells, and culture was continued at 37° C. in the presence of 10% $CO_2$ for 8 hr. Thereafter, the medium of the aforementioned cells was exchanged with a fresh medium.

2-b: Transfection of Sponge Oligo, Monomer Decoy or LNA to HCT116 Cells

HCT116 cells transfected with the aforementioned reporter gene were recovered, and plated on a 24 well dish at $5 \times 10^4$/well. Then, the cells transfected with the aforementioned pGL4-NTC and pMIR-REPORT and the cells transfected with the aforementioned pGL4-miR16 and pMIR-REPORT were each transfected with sponge oligo, monomer decoy or LNA. First, the aforementioned 10 µM sponge oligo solution, the aforementioned LNA solution (1.25 µL), or the aforementioned 10 µM monomer decoy solution (3.75 µL) was added to OptiMEM (50 µL) to prepare solution C. In addition, Lipofectamine RNAiMAX (Invitrogen, 2 µL) was added to OptiMEM (50 µL) to prepare solution D. Solution C and solution D were each stood at room temperature for 5 min, solution C and solution D were mixed, and stood at room temperature for 20 min, during which time the medium of the aforementioned plated cells was exchanged with a fresh medium. After 20 min, the mixture of the aforementioned solution C and solution D was added to the aforementioned culture medium containing HCT116 cells transfected with the aforementioned reporter gene, and culture was continued at 37° C. in the presence of 10% $CO_2$ for 24 hr. Thereafter, the medium of the aforementioned cells was exchanged with a fresh medium. By the transfection, the final concentration of sponge oligo or LNA was 25 nM, and the final concentration of the monomer decoy was 75 nM.

2-c: Activity Measurement

After 48 hr from the transfection of the aforementioned sponge oligo, monomer decoy or LNA, the luciferase activity of each cell was measured by Dual-Luciferase (registered trade mark) Reporter Assay System (Promega KK) according to the attached protocol. The measurement device used was Berthold Centro 960 (Berthold).

2-d: Analysis of Activity

As mentioned above, pMIR-REPORT-derived firefly luciferase reflects the transfection efficiency, and pGL4-NTC and pGL4-miR16-derived Renilla luciferase reflects the miR-16 activity. Therefore, the normalized Renilla luciferase activity value is obtained by dividing the activity value ($A_{pGL4-NTC}$ or $A_{pGL4-miR16}$) of Renilla luciferase by the activity value ($A_{pMIR-REPORT(NTC)}$ or $A_{pMIR-REPORT(miR-16)}$) of firefly luciferase. The activity value of Renilla luciferase derived from pGL4-miR16 based on the normalized activity value of Renilla luciferase derived from pGL4-NTC as 1 is the value suppressed by miR-16. Thus, the value of miR-16 activity-suppressive effect was obtained by the following calculation formula for each of sponge oligo, monomer decoy and LNA.

value of miR-16 activity-suppressive effect =

$$\frac{A_{pGL4-miR16} / A_{pMTR-REPORT(miR-16)}}{A_{pGL4-NTC} / A_{pMIR-REPORT(NTC)}}$$

(3) Results

Figure 7:
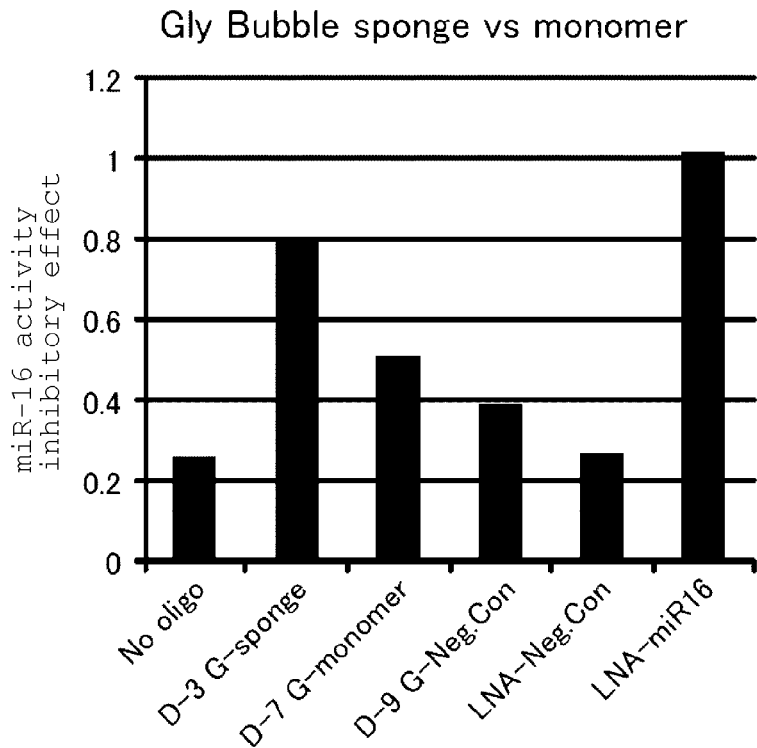
FIG. 7 is a graph showing the miR-16 activity-suppressive effect of the microRNA inhibitor of Example 2-1.
Figure 8:
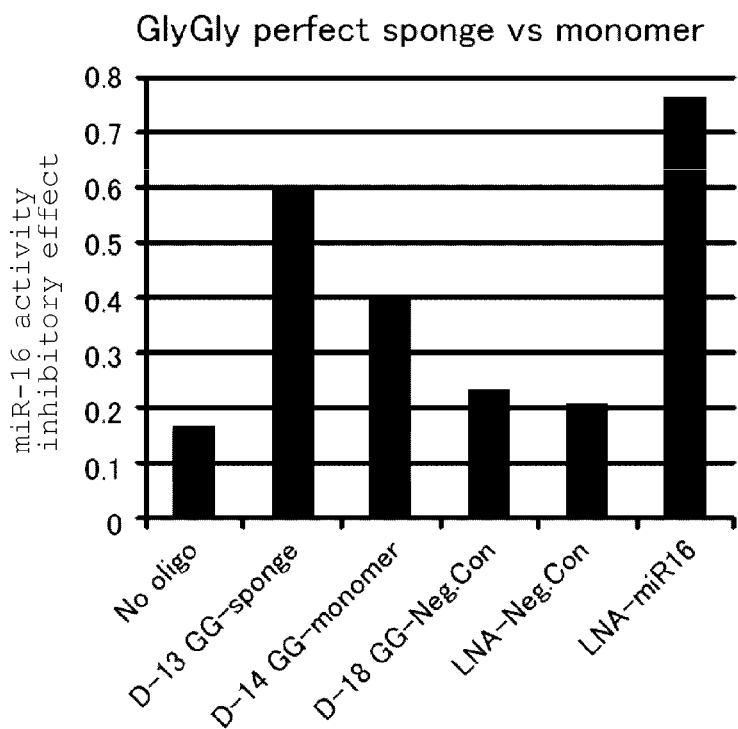
FIG. 8 is a graph showing the miR-16 activity-suppressive effect of the microRNA inhibitor of Example 2-2.
Figure 9:
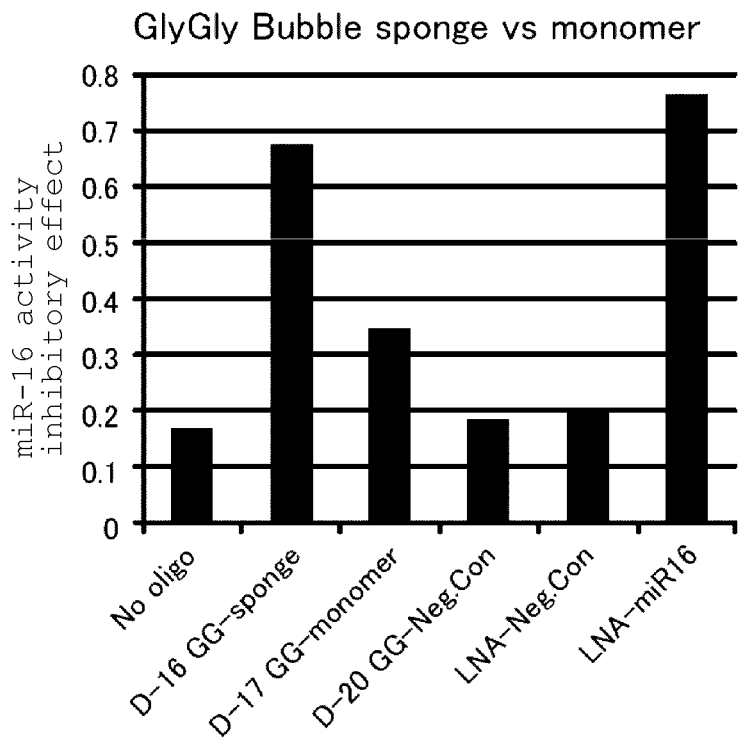
FIG. 9 is a graph showing the miR-16 activity-suppressive effect of the microRNA inhibitor of Example 2-3.

The obtained results are shown in FIGS. 7-9. The vertical axis in FIGS. 7-9 shows the miR-16 activity-suppressive effect (also referred to as activity inhibitory effect or activity suppressing ability). The same applies to the below-mentioned FIGS. 10-21. FIG. 7 shows the results obtained by using Gly-containing Bubble type sponge oligo (Example 2-1), FIG. 8 shows the results obtained by using GlyGly-containing Perfect type sponge oligo (Example 2-2), and FIG. 9 shows the results obtained by using GlyGly-containing Bubble type sponge oligo (Example 2-3). As shown in the Figures, in all cases, sponge oligo was shown to have a miR-16 activity suppressing ability comparable to that of LNA. Furthermore, the sponge oligo of this Example is advantageous in that, due to the structure thereof, it is extremely superior in convenience and has highly broad utility as compared to LNA. In this Example, monomer decoy was used at a concentration 3-fold that of sponge oligo to give the same number of sequences bound to miR-16, for sponge oligo and monomer decoy; however, sponge oligo showed a higher miR-16 activity suppressing ability than monomer decoy. This indicates that coordinated binding of miRNA occurs on sponge oligo.

Example 3

Suppressive Effect of DNA Type Sponge Oligo and RNA Type Sponge Oligo on miR-16 Activity in HCT116 Cells (1) Material 1-a: Oligonucleotide As shown in the below-mentioned sequence and Table 2 below, microRNA inhibitors wherein sequences complementary to the sequence of miR-16 (microRNA) were linked by GlyGly (the aforementioned G2) were used to measure their microRNA suppressive effect (microRNA inhibitory activity).

```
(Example 3-1)
spo-D-16 (GlyGly-containing Bubble type DNA sponge
oligo)
                                        (SEQ ID NO: 6)
5'-GlyGly-CGCCAATATTCGATGCTGCTA-GlyGly-CGCCAATATTC
GATGCTGCTA-GlyGly-CGCCAATATTCGATGCTGCTA-
GlyGly-T-3'

(Example 3-2)
spo-R-16 (GlyGly-containing Bubble type RNA sponge
oligo)
                                       (SEQ ID NO: 13)
5'-GlyGly-CGCCAAUAUUCGAUGCUGCUA-GlyGly-CGCCAAUAUUC
GAUGCUGCUA-GlyGly-CGCCAAUAUUCGAUGCUGCUA-
GlyGly-U-3'
```

The following negative control oligo was used for each of them.

```
(Reference Example 3-1)
spo-D-20 (GlyGly-containing Bubble type DNA sponge
oligo negative control)
                                       (SEQ ID NO: 10)
5'-GlyGly-CGCCAATATTCCATTATAAGA-GlyGly-CGCCAATATTC
CATTATAAGA-GlyGly-CGCCAATATTCCATTATAAGA-
GlyGly-T-3'

(Reference Example 3-2)
spo-R-20 (GlyGly-containing Bubble type RNA sponge
oligo negative control)
                                       (SEQ ID NO: 14)
5'-GlyGly-CGCCAAUAUUCCAUUAUAAGA-GlyGly-CGCCAAUAUUC
CAUUAUAAGA-GlyGly-CGCCAAUAUUCCAUUAUAAGA-
GlyGly-U-3'
```

Furthermore, as the microRNA inhibitors of the following Reference Examples 3-3 and 3-4, the positive control (LNA-miR16) of the suppressive effect on miR-16 activity, and the following LNA molecule (manufactured by EXIQON) which is a negative control thereof (LNA-Neg.Con) were used. Reference Example 3-3 is the same as the aforementioned Reference Example 2-7, and Reference Example 3-4 is the same as the aforementioned Reference Example 2-8.

```
(Reference Example 3-3)
LNA-miR16
                                       (SEQ ID NO: 11)
GCCAATATTTACGTGCTGCT (Reference Example 3-4)
LNA-Neg.Con
                                       (SEQ ID NO: 12)
AGAGCTCCCTTCAATCCAAA
```

The above-mentioned aqueous oligonucleotide solutions were prepared with distilled water for injection to 10 μM.

TABLE 2

| Example 3-1 | spo-D-16 (D-16 DNA-sponge) | GlyGly-containing Bubble type sponge oligo(DNA) |
| Example 3-2 | spo-R-16 (D-16 RNA-sponge) | GlyGly-containing Bubble type sponge oligo(RNA) |
| Reference Example 3-1 | spo-D-20 (D-20 Neg. Con) | GlyGly-containing Bubble type sponge oligo Neg. Con |
| Reference Example 3-2 | spo-R-20 (R-20 Neg. Con) | GlyGly-containing Bubble type sponge oligo Neg. Con |
| Reference Example 3-3 | LNA-miR16 | |
| Reference Example 3-4 | LNA-Neg. Con | |

1-b: Cell Line

The cell line and medium used were the same as those in Example 2.

1-c: Reporter Plasmid

As the reporter plasmid, a plasmid containing the same reporter gene as in Example 2 was used.

(2) Method 2-a: Transfection of Reporter Gene to HCT116 Cells

Using HCT116 cells and in the same manner as in Example 2, reporter gene plasmid pGL4-NTC (2 μg) and pMIR-REPORT (2 μg), or pGL4-miR16 (2 μg) and pMIR-REPORT (2 μg) were each transfected to HCT116 cells.

2-b: Transfection of Sponge Oligo, LNA to Cells

Sponge oligo or LNA was transfected to the cells, transfected with the aforementioned reporter gene, by a method similar to Example A2. As a result of the transfection, the final concentration of sponge oligo and LNA was 25 nM.

2-c: Activity Measurement

After 48 hr from the transfection of the aforementioned sponge oligo or LNA, the luciferase activity of each cell was measured by Dual-Luciferase (registered trade mark) Reporter Assay System (Promega KK) according to the attached protocol. The measurement device used was Berthold Centro 960 (Berthold).

2-d: Analysis of Activity

By a method similar to that in Example 2, the value of miR-16 activity-suppressive effect was obtained.

(3) Results

Figure 10:
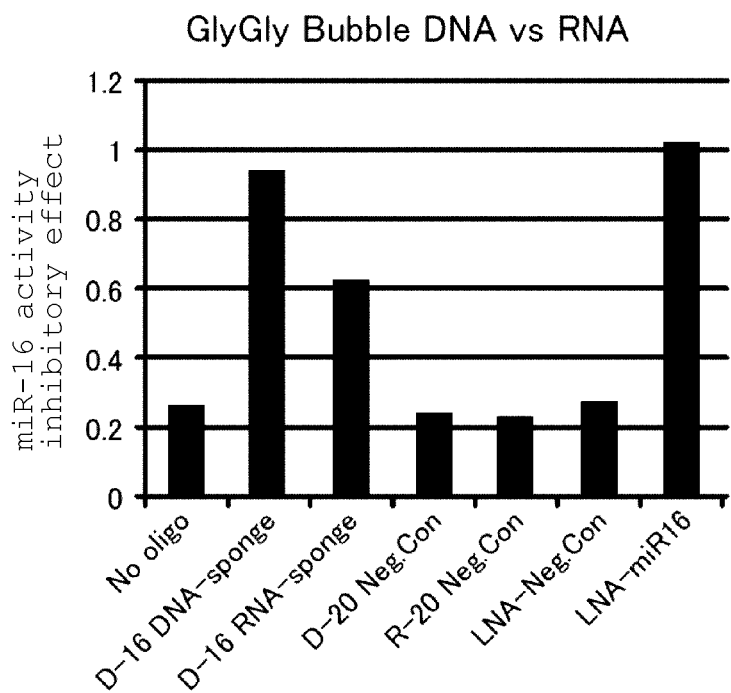
FIG. 10 is a graph showing the miR-16 activity-suppressive effect of the microRNA inhibitor of Example 3.

The obtained results are shown in FIG. 10. As shown in the Figure, both the DNA type sponge oligo and the RNA type sponge oligo of the Example showed an extremely high miR-16 activity suppressing ability as compared to the negative control. Furthermore, the DNA type sponge oligo and the RNA type sponge oligo of the Example are advantageous in that, due to the structures thereof, they are extremely superior in convenience and have highly broad utility as compared to LNA. In addition, the DNA type sponge oligo of this Example showed a higher miR-16 activity suppressing ability than the RNA type sponge oligo, and had a high miR-16 activity suppressing ability comparable to that of LNA.

In this Example, as mentioned above, the DNA type sponge oligo showed a higher microRNA activity-suppressive effect than the RNA type sponge oligo. In the present invention, the RNA type sponge oligo possibly has a higher microRNA activity suppressing ability than the DNA type sponge oligo, depending on the kind of the target miRNA, or when the cell line is different from that in this Example and the like.

Example 4

Comparison of miR-16 Activity-Suppressive Effect of Sponge Oligo Having Different Linker Molecule in HCT116 Cells and HEK293T Cells (1) Material 1-a: Oligonucleotide As shown in the below-mentioned base sequence and Table 3 below, a microRNA inhibitor wherein a sequence complementary to the sequence of miR-16 was linked by Gly (the aforementioned G1), GlyGly (the aforementioned G2) or TPA was used to measure the microRNA suppressive effect (microRNA inhibitory activity).

(Example 4-1)
spo-D-3 (Gly-containing Bubble type sponge oligo)
(SEQ ID NO: 2)
5'-Gly-CGCCAATATTCGATGCTGCTA-Gly-CGCCAATATTCGATGCT
GCTA-Gly-CGCCAATATTCGATGCTGCTA-Gly-T-3'

(Example 4-2)
spo-D-16 (GlyGly-containing Bubble type sponge oligo)
(SEQ ID NO: 6)
5'-GlyGly-CGCCAATATTCGATGCTGCTA-GlyGly-CGCCAATATTC
GATGCTGCTA-GlyGly-CGCCAATATTCGATGCTGCTA-
GlyGly-T-3'

(Example 4-3)
spo-D-13 (GlyGly-containing Perfect type sponge oligo)
(SEQ ID NO: 4)
5'-GlyGly-CGCCAATATTTACGTGCTGCTA-GlyGly-CGCCAATATT
TACGTGCTGCTA-GlyGly-CGCCAATATTTACGTGCTGCTA-
GlyGly-T-3'

(Example 4-4)
spo-D-15 (TPA-containing Perfect type sponge oligo)
(SEQ ID NO: 15)
5'-TPA-CGCCAATATTTACGTGCTGCTA-TPA-CGCCAATATTTACGTG
CTGCTA-TPA-CGCCAATATTTACGTGCTGCTA-TPA-T-3'

(Example 4-5)
spo-D-21 (TPA-containing Bubble type sponge oligo)
(SEQ ID NO: 16)
5'-TPA-CGCCAATATTCGATGCTGCTA-TPA-CGCCAATATTCGATGCT
GCTA-TPA-CGCCAATATTCGATGCTGCTA-TPA-T-3'

(Example 4-6)
spo-D-22 (TPA-containing Bulge type sponge oligo)
(SEQ ID NO: 17)
5'-TPA-CGCCAATATTAGTTCCGTGCTGCTA-TPA-
CGCCAATATTAGTTCCGTGCTGCTA-TPA-CGCCAATATTAGTTCCGT
GCTGCTA-TPA-T-3'

(Example 4-7)
spo-D-23 (GlyGly-containing Bulge type sponge oligo)
(SEQ ID NO: 18)
5'-GlyGly-CGCCAATATTAGTTCCGTGCTGCTA-GlyGly-
CGCCAATATTAGTTCCGTGCTGCTA-GlyGly-CGCCAATATTAGTTC
CGTGCTGCTA-GlyGly-T-3'

As negative control oligo for the aforementioned Examples 4-1-4-7, microRNA inhibitors (the following Reference Examples 4-1-4-4) wherein the following base sequences were linked by Gly (the aforementioned G1) or GlyGly (the aforementioned G2) were used to measure the microRNA suppressive effect (microRNA inhibitory activity).

(Reference Example 4-1)
spo-D-9 (Gly-containing Bubble type sponge oligo negative control)
(SEQ ID NO: 8)
5'-Gly-CGCCAATATTCCATTATAAGA-Gly-CGCCAATATTCCATTAT
AAGA-Gly-CGCCAATATTCCATTATAAGA-Gly-T-3'

(Reference Example 4-2)
spo-D-20 (GlyGly-containing Bubble type sponge oligo negative control)
(SEQ ID NO: 10)
5'-GlyGly-CGCCAATATTCCATTATAAGA-GlyGly-CGCCAATATTC
CATTATAAGA-GlyGly-CGCCAATATTCCATTATAAGA-
GlyGly-T-3'

(Reference Example 4-3)
spo-D-18 (GlyGly-containing Perfect type sponge oligo negative control)
(SEQ ID NO: 9)
5'-GlyGly-CGCCAATATTTACGTAATTACA-GlyGly-CGCCAATATT
TACGTAATTACA-GlyGly-CGCCAATATTTACGTAATTACA-
GlyGly-T-3'

(Reference Example 4-4)
spo-D-19 (TPA-containing Perfect type sponge oligo negative control)
(SEQ ID NO: 19)
5'-TPA-CGCCAATATTTACGTAATTACA-TPA-CGCCAATATTTACGTA
ATTACA-TPA-CGCCAATATTTACGTAATTACA-TPA-T-3'

Furthermore, as the microRNA inhibitors of the following Reference Examples 4-5 and 4-6, the positive control (LNA-miR16) of the suppressive effect on miR-16 activity, and the following LNA molecule (manufactured by EXIQON) which is a negative control thereof (LNA-Neg.Con) were used. Reference Example 4-5 is the same as the aforementioned Reference Example 2-7, and Reference Example 4-6 is the same as the aforementioned Reference Example 2-8.

(Reference Example 4-5)
LNA-miR16
(SEQ ID NO: 11)
GCCAATATTTACGTGCTGCT (Reference Example 4-6)
LNA-Neg.Con
(SEQ ID NO: 12)
AGAGCTCCCTTCAATCCAAA The above-mentioned oligonucleotides were dissolved in distilled water for injection to 10 μM, whereby RNA solutions were prepared.

TABLE 3

| Example 4-1 | spo-D-3 (D-3 G-sponge) | Gly-containing Bubble type sponge oligo |
|---|---|---|
| Example 4-2 | spo-D-16 (D-16 GG-sponge) | GlyGly-containing Bubble type sponge oligo |
| Example 4-3 | spo-D-13 (D-13 G-sponge) | GlyGly-containing Perfect type sponge oligo |
| Example 4-4 | spo-D-15 (D-15 TPA-sponge) | TPA-containing Perfect type sponge oligo |
| Example 4-5 | spo-D-21 (D-21 TPA-sponge) | TPA-containing Bubble type sponge oligo |
| Example 4-6 | spo-D-22 (D-22 TPA-sponge) | TPA-containing Bulge type sponge oligo |
| Example 4-7 | spo-D-23 (D-23 GG-sponge) | GlyGly-containing Bulge type sponge oligo |
| Reference Example 4-1 | spo-D-9 (D-9 G-Neg. Con) | Gly-containing Bubble type sponge oligo Neg. Con |
| Reference Example 4-2 | spo-D-20 (D-20 GG-Neg. Con) | GlyGly-containing Bubble type sponge oligo Neg. Con |
| Reference Example 4-3 | spo-D-18 (D-18 GG-Neg. Con) | GlyGly-containing Perfect type sponge oligo Neg. Con |
| Reference Example 4-4 | spo-D-19 (D-19 TPA-Neg. Con) | TPA-containing Perfect type sponge oligo Neg. Con |
| Reference Example 4-5 | LNA-miR16 | |
| Reference Example 4-6 | LNA-Neg. Con | |

1-b: Cell Line and Medium

The cell line used was human colon cancer cell line HCT116 (ATCC) or human embryonic kidney cell line HEK293T (ATCC). As the medium, DMEM medium containing 10% FBS (Nacalai) was used for culture at 37° C. in the presence of 10% $CO_2$.

1-c: Reporter Plasmid

As the reporter plasmid, a plasmid containing the same reporter gene as in Example 2 was used.

(2) Method
2-a: Transfection of Reporter Gene to HCT116 Cells or HEK293T Cells

Using HCT116 cells or 293T cells and in the same manner as in Example 2, reporter gene plasmid pGL4-NTC (2 μg) and pMIR-REPORT (2 μg), or pGL4-miR16 (2 μg) and pMIR-REPORT (2 μg) were each transfected.

2-b: Transfection of Sponge Oligo or LNA to HCT116 Cells or HEK293T cells

Sponge oligo or LNA was transfected to the cells, transfected with the aforementioned reporter gene, by a method similar to Example A2. As a result of the transfection, the final concentration of sponge oligo and LNA was 25 nM.

2-c: Activity Measurement

After 48 hr from the transfection of the aforementioned sponge oligo or LNA to the aforementioned HCT116 cells or HEK293T cells, the luciferase activity of each cell was measured by Dual-Luciferase (registered trade mark) Reporter Assay System (Promega KK) according to the attached protocol. The measurement device used was Berthold Centro 960 (Berthold).

2-d: Analysis of Activity

By a method similar to that in Example 2, the value of miR-16 activity-suppressive effect was obtained.

(3) Results

Figure 11:
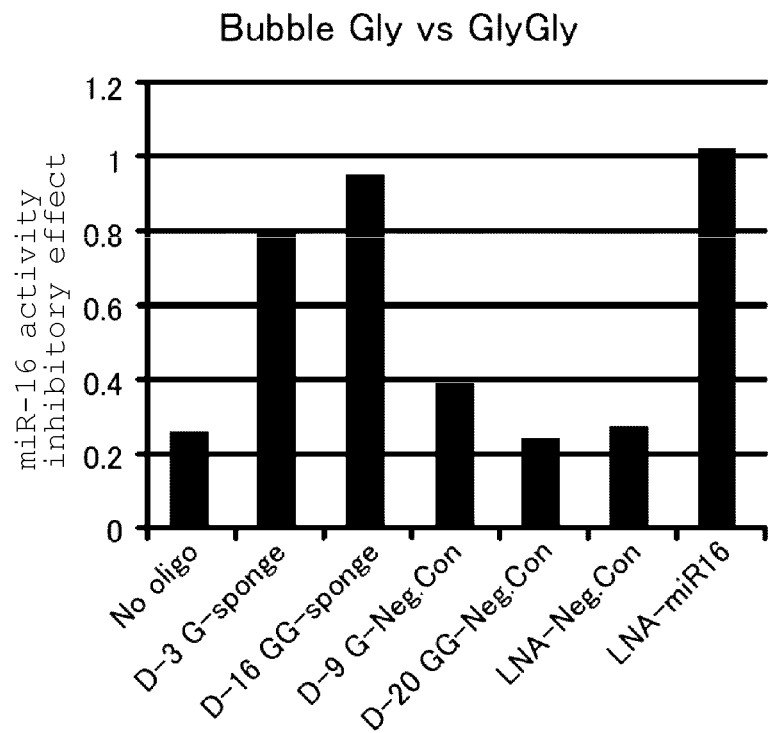
FIG. 11 is a graph showing comparison of the miR-16 activity-suppressive effects of Gly type sponge oligo(microRNA inhibitor) and GlyGly type sponge oligo(microRNA inhibitor) by using HCT116 cells in Example 4.
Figure 12:
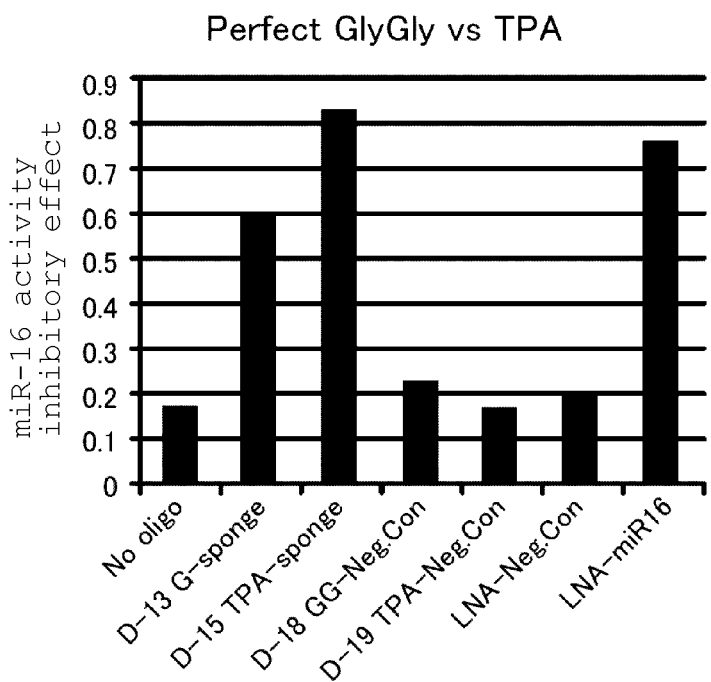
FIG. 12 is a graph showing comparison of the miR-16 activity-suppressive effects of GlyGly type sponge oligo(microRNA inhibitor) and TPA type sponge oligo(microRNA inhibitor) by using HCT116 cells in Example 4.
Figure 13:
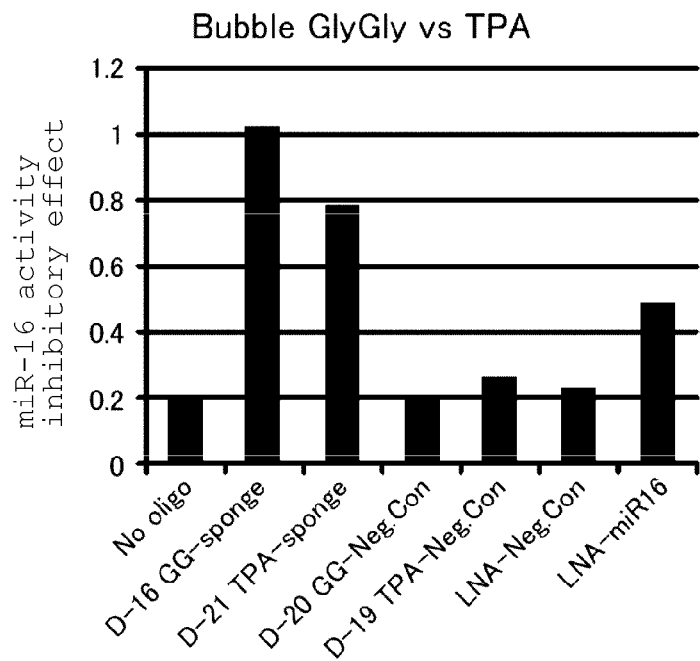
FIG. 13 is another graph showing comparison of the miR-16 activity-suppressive effects of GlyGly type sponge oligo (microRNA inhibitor) and TPA type sponge oligo(microRNA inhibitor) by using HCT116 cells in Example 4.
Figure 14:
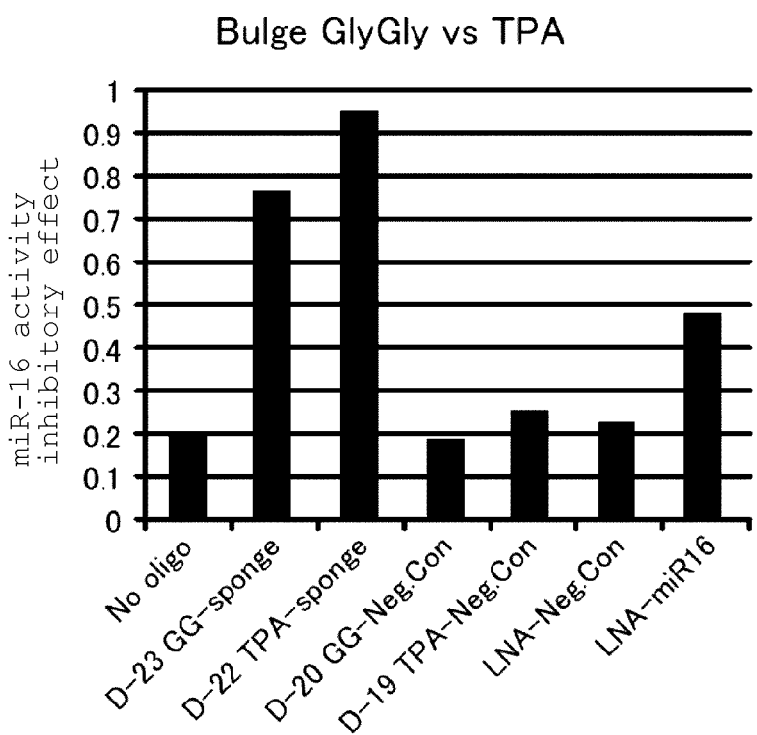
FIG. 14 is yet another graph showing comparison of the miR-16 activity-suppressive effects of GlyGly type sponge oligo(microRNA inhibitor) and TPA type sponge oligo(microRNA inhibitor) by using HCT116 cells in Example 4.
Figure 15:
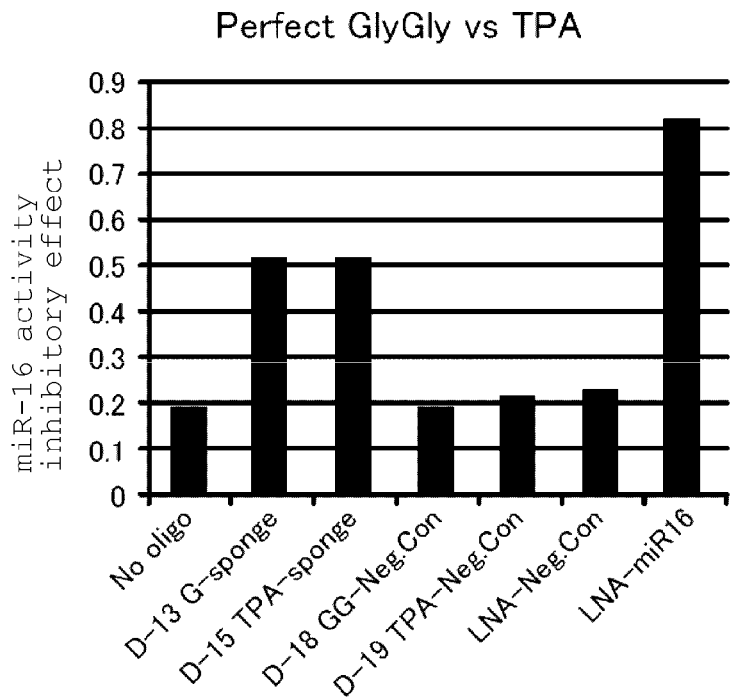
FIG. 15 is a graph showing comparison of the miR-16 activity-suppressive effects of Gly type sponge oligo(microRNA inhibitor) and GlyGly type sponge oligo(microRNA inhibitor) by using HEK293T cells in Example 4.
Figure 16:
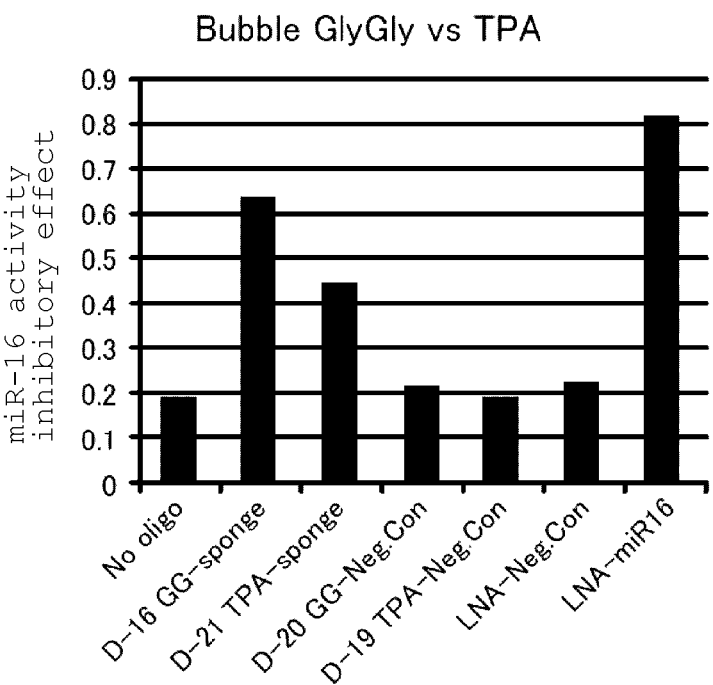
FIG. 16 is another graph showing comparison of the miR-16 activity-suppressive effects of Gly type sponge oligo(microRNA inhibitor) and GlyGly type sponge oligo(microRNA inhibitor) by using HEK293T cells in Example 4.
Figure 17:
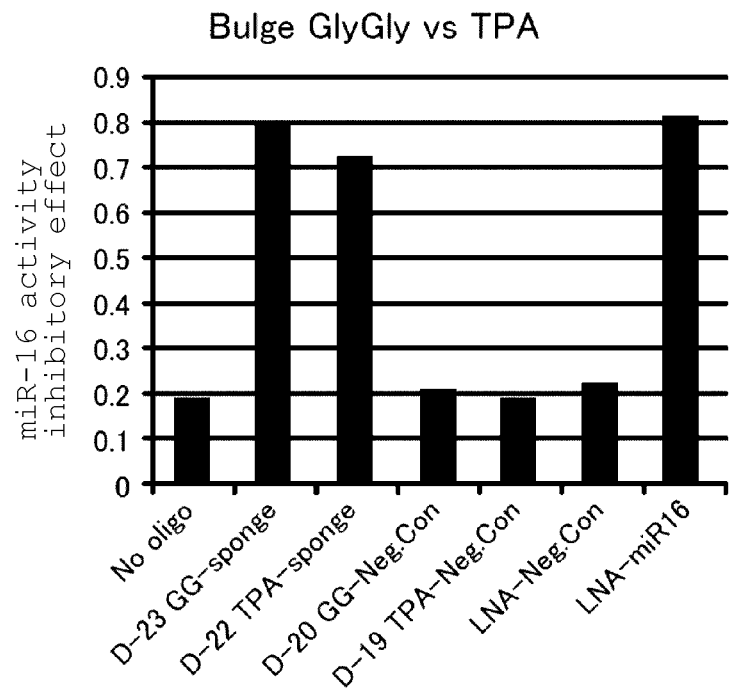
FIG. 17 is a still another graph showing comparison of the miR-16 activity-suppressive effects of Gly type sponge oligo (microRNA inhibitor) and GlyGly type sponge oligo(microRNA inhibitor) by using HEK293T cells in Example 4.

The obtained results are shown in FIG. 11 to FIG. 17. FIG. 11 shows comparison of Gly type sponge oligo and GlyGly type sponge oligo by using HCT116 cells. As a result, it was found that the GlyGly type sponge oligo has a little stronger suppressive effect than the Gly type. FIG. 12 to FIG. 17 show comparison of the GlyGly type sponge oligo and the TPA type sponge oligo. In FIG. 12 to FIG. 14, HCT116 cells were used, and FIG. 15 to FIG. 17 show the results obtained by using HEK293T cells. When perfect type sponge oligo was used, TPA type showed higher activity in HCT116 cells (FIG. 12), and the activities of the two were almost the same in HEK293T cells (FIG. 15). When bubble type sponge oligo was used, GlyGly type showed a higher activity in both HCT116 cells and HEK293T cells (FIGS. 13 and 16). When Bulge type sponge oligo was used, TPA type showed higher activity in HCT116 cells (FIG. 14), and GlyGly type showed higher activity in HEK293T cells (FIG. 17). From the above results, it was confirmed that, in the sponge oligo of this Example, TPA type and GlyGly type showed a little stronger suppressive effect than Gly type on the miR-16 activity in vitro. There was almost no difference in the miR-16 activity-suppressive effect of TPA type and GlyGly type.

Example 5

Comparison of miR-16 Activity-Suppressive Effect of Sponge Oligo Having Different miR-16 Binding Sequence in HCT116 Cells and HEK293T Cells (1) Material
1-a: Oligonucleotide As shown in the below-mentioned base sequences and Table 4 below, microRNA inhibitors wherein sequences complementary to the sequence of miR-16 were linked by TPA were used to measure their microRNA suppressive effect (microRNA inhibitory activity).

(Example 5-1)
spo-D-15 (TPA-containing Perfect type sponge oligo)
(SEQ ID NO: 15)
5'-TPA-CGCCAATATTTACGTGCTGCTA-TPA-CGCCAATATTTACGTG CTGCTA-TPA-CGCCAATATTTACGTGCTGCTA-TPA-T-3'

(Example 5-2)
spo-D-21 (TPA-containing Bubble type sponge oligo)
(SEQ ID NO: 16)
5'-TPA-CGCCAATATTCGATGCTGCTA-TPA-CGCCAATATTCGATGCT GCTA-TPA-CGCCAATATTCGATGCTGCTA-TPA-T-3'

(Example 5-3)
spo-D-22 (TPA-containing Bulge type sponge oligo)
(SEQ ID NO: 17)
5'-TPA-CGCCAATATTTAGTTCCGTGCTGCTA-TPA-CGCCAATATTTAGTTCCGTGCTGCTA-TPA-CGCCAATATTTAGTTCCGT GCTGCTA-TPA-T-3'

As negative control oligo for the aforementioned Examples 5-1-5-3, the microRNA inhibitor of the following Reference Example 5-1 was used to measure the microRNA suppressive effect (microRNA inhibitory activity).

(Reference Example 5-1)
spo-D-19 (TPA-containing Perfect type sponge oligo negative control)
(SEQ ID NO: 19)
5'-TPA-CGCCAATATTTACGTAATTACA-TPA-CGCCAATATTTACGTA ATTACA-TPA-CGCCAATATTTACGTAATTACA-TPA-T-3'

Furthermore, as the microRNA inhibitors of the following Reference Examples 5-2 and 5-3, the positive control (LNA-miR16) of the suppressive effect on miR-16 activity, and the following LNA molecule (manufactured by EXIQON) which is a negative control thereof (LNA-Neg.Con) were used. Reference Example 5-2 is the same as the aforementioned Reference Example 2-7, and Reference Example 5-3 is the same as the aforementioned Reference Example 2-8.

(Reference Example 5-2)
LNA-miR16
(SEQ ID NO: 11)
GCCAATATTTACGTGCTGCT (Reference Example 5-3)
LNA-Neg.Con
(SEQ ID NO: 12)
AGAGCTCCCTTCAATCCAAA The above-mentioned aqueous oligonucleotide solutions were prepared with distilled water for injection to 10 μM.

TABLE 4

| Example 5-1 | spo-D-15 (D-15 Perfect sponge) | TPA-containing Perfect type sponge oligo |
|---|---|---|
| Example 5-2 | spo-D-21 (D-21 Bubble sponge) | TPA-containing Bubble type sponge oligo |
| Example 5-3 | spo-D-22 (D-22 Bulge sponge) | TPA-containing Bulge type sponge oligo |
| Reference Example 5-1 | spo-D-19 (D-19 TPA-Neg. Con) | TPA-containing Perfect type sponge oligo Neg. Con |
| Reference Example 5-2 | LNA-miR16 | |
| Reference Example 5-3 | LNA-Neg. Con | |

1-b: Cell Line

The same cell line as in Example 4 was used for the activity measurement.

1-c: Reporter Plasmid

As the reporter plasmid, a plasmid containing the same reporter gene as in Example 2 was used.

(2) Method
2-a: Transfection of Reporter Gene to HCT116 Cells or HEK293T Cells

Using HCT116 cells or 293T cells and in the same manner as in Example A2, reporter gene plasmid pGL4-NTC (2 μg)

and pMIR-REPORT (2 μg), or pGL4-miR16 (2 μg) and pMIR-REPORT (2 μg) were each transfected to HCT116 cells or HEK293T cells.

2-b: Transfection of Sponge Oligo or LNA to HCT116 Cells or HEK293T Cells

Sponge oligo or LNA was transfected to the cells, transfected with the aforementioned reporter gene, by a method similar to Example A2. As a result of the transfection, the final concentration of sponge oligo and LNA was 25 nM.

2-c: Activity Measurement

After 48 hr from the transfection of the sponge oligo or LNA, the luciferase activity of each cell was measured by Dual-Luciferase (registered trade mark) Reporter Assay System (Promega KK) according to the attached protocol. The measurement device used was Berthold Centro 960 (Berthold).

2-d: Analysis of Activity

By a method similar to that in Example 2, the value of miR-16 activity-suppressive effect was obtained.

(3) Results

Figure 18:
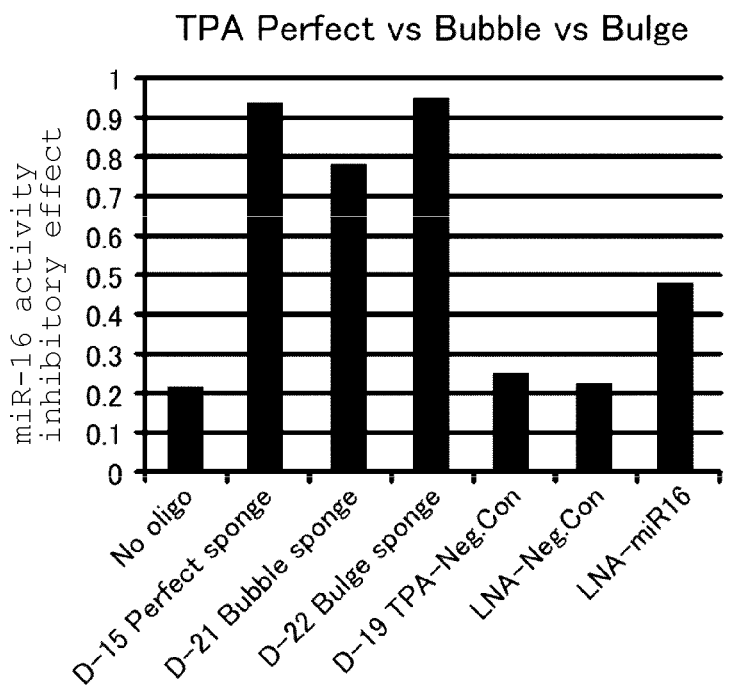
FIG. 18 is a graph showing comparison of the miR-16 activity-suppressive effects of sponge oligo(microRNA inhibitor) when miR-16 binding sequence is of a Perfect type, Bubble type or Bulge type by using HCT116 cells in Example 5.
Figure 19:
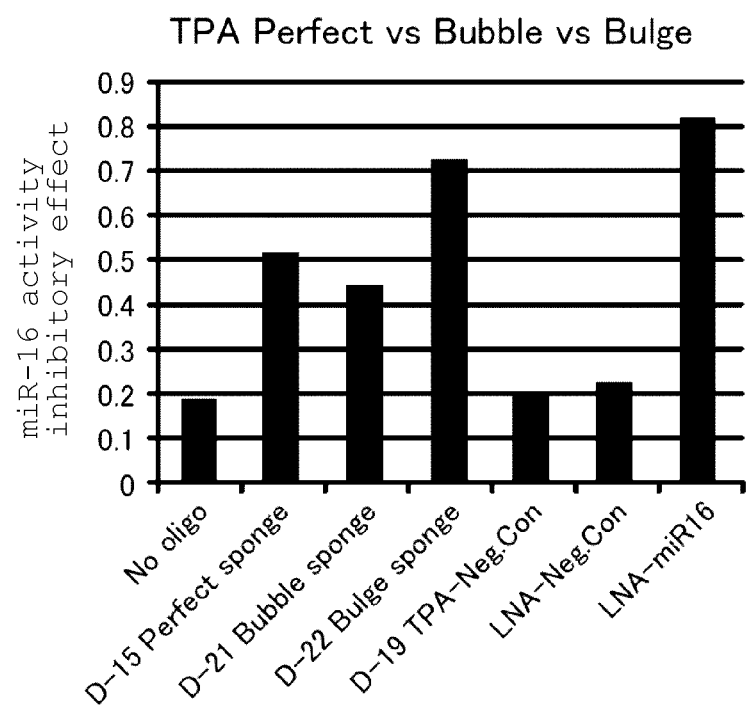
FIG. 19 is a graph showing comparison of the miR-16 activity-suppressive effects of sponge oligo(microRNA inhibitor) when miR-16 binding sequence is of a Perfect type, Bubble type or Bulge type by using HEK293T cells in Example 5.

The obtained results are shown in FIGS. 18 and 19. FIG. 18 shows comparison of sponge oligo activity when the miR-16 binding sequence is Perfect type, Bubble type, or Bulge type, by using HCT116 cells. As a result, these three showed almost no difference but Perfect type and Bulge type showed a comparatively strong suppressive effect on the miR-16 activity in vitro. FIG. 19 shows comparison of sponge oligo activity when the miR-16 binding sequence is Perfect type, Bubble type, or Bulge type, by using HEK293T cells. As a result, among these three, Bulge type showed the strongest suppressive effect on the miR-16 activity in vitro.

While the present invention has been explained by referring to the embodiments, the present invention is not limited by the above-mentioned embodiments. The constitution and detail of the present invention can be variously changed within the scope of the present invention as long as those of ordinary skill in the art can understand.

This application is based on a patent application No. 2012-047466 filed in Japan (filing date: Mar. 4, 2012), the contents of which are incorporated in full herein.

INDUSTRIAL APPLICABILITY

Since the microRNA inhibitor of the present invention does not require use of a special modified nucleic acid, it is superior in broad utility, and difficult to degrade since the aforementioned complementary sequences are linked (bonded) via a linker residue. Therefore, the microRNA inhibitor of the present invention can be widely used in various fields.

EXPLANATION OF SYMBOLS 1 microRNA inhibitor
2 complementary sequence
3 the linker residue

The invention claimed is:

1. A microRNA inhibitor comprising two or more sequences complementary to a sequence of a microRNA to be the target of inhibition, wherein said two or more complementary sequences are linked via linker residue(s), wherein the linker residue is bonded to each terminal portion of said complementary sequences present at both termini of the microRNA inhibitor, and wherein the linker residue is selected from the group consisting of (a) an atomic group represented by the following chemical formula (G1):

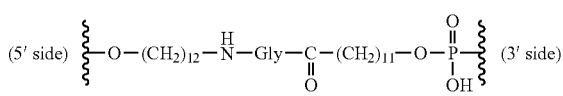

(G1)

wherein Gly in the chemical formula (G1) is an atomic group represented by the following chemical formula (Gly): —HN—CH$_2$—CO—, wherein the terminal carbonyl carbon in the chemical formula (Gly) is bonded to the N atom in the chemical formula (G1), and wherein the terminal nitrogen atom in the chemical formula (Gly) is bonded to the carbonyl carbon in the chemical formula (G1), (b) an atomic group represented by the following chemical formula (G2):

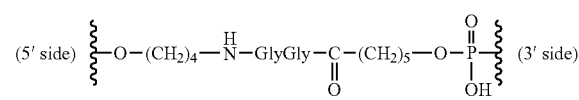

(G2)

wherein GlyGly in the chemical formula (G2) is an atomic group represented by the following chemical formula (GlyGly): —HN—CH$_2$—CO—HN—CH$_2$—CO—, wherein the terminal carbonyl carbon in the chemical formula (GlyGly) is bonded to the N atom in the chemical formula (G2), and wherein the terminal nitrogen atom in the chemical formula (GlyGly) is bonded to the carbonyl carbon in the chemical formula (G2), and (c) an atomic group represented by the following chemical formula (TPA):

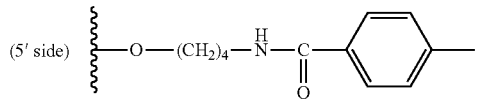

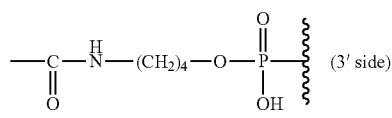

(TPA)

provided that when the linker residue is present at the terminal portion of the complementary sequence of the aforementioned microRNA present at the terminus, a terminal of the linker residue is H, a protecting group, or a phosphate-protecting group.

2. The microRNA inhibitor according to claim 1, which is represented by any of the following SEQ ID NOs: 2, 4, 6, 13 and 15-18:

```
                                          (SEQ ID NO: 2)
5'-Gly-CGCCAATATTCGATGCTGCTA-Gly-CGCCAATATTCGATGCT
GCTA-Gly-CGCCAATATTCGATGCTGCTA-Gly-T-3'

(SEQ ID NO: 4)
5'-GlyGly-CGCCAATATTTACGTGCTGCTA-GlyGly-
CGCCAATATTTACGTGCTGCTA-GlyGly-CGCCAATATTTACGTGCTGC
TA-GlyGly-T-3'

(SEQ ID NO: 6)
5'-GlyGly-CGCCAATATTCGATGCTGCTA-GlyGly-
CGCCAATATTCGATGCTGCTA-GlyGly-CGCCAATATTCGATGCTG
CTA-GlyGly-T-3'

(SEQ ID NO: 13)
5'-GlyGly-CGCCAAUAUUCGAUGCUGCUA-GlyGly-
CGCCAAUAUUCGAUGCUGCUA-GlyGly-CGCCAAUAUUCGAUGCUG
CUA-GlyGly-U-3'

(SEQ ID NO: 15)
5'-TPA-CGCCAATATTTACGTGCTGCTA-TPA-
CGCCAATATTTACGTGCTGCTA-TPA-CGCCAATATTTACGTGCTGCTA-
TPA-T-3'

(SEQ ID NO: 16)
5'-TPA-CGCCAATATTCGATGCTGCTA-TPA-CGCCAATATTCGATGCT
GCTA-TPA-CGCCAATATTCGATGCTGCTA-TPA-T-3'

(SEQ ID NO: 17)
5'-TPA-CGCCAATATTTAGTTCCGTGCTGCTA-TPA-
CGCCAATATTTAGTTCCGTGCTGCTA-TPA-
CGCCAATATTTAGTTCCGTGCTGCTA-TPA-T-3'

(SEQ ID NO: 18)
5'-GlyGly-CGCCAATATTTAGTTCCGTGCTGCTA-GlyGly-
CGCCAATATTTAGTTCCGTGCTGCTA-GlyGly-
CGCCAATATTTAGTTCCGTGCTGCTA-GlyGly-T-3'
``` wherein in the sequence shown by SEQ ID NO: 2, Gly is an atomic group represented by the following chemical formula (G1), and when no base is bonded to the 5' terminus, a hydrogen atom (H) is bonded to the 5' terminus:

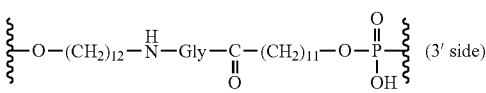

(G1)

wherein in the chemical formula (G1), Gly is an atomic group represented by the following chemical formula (Gly): —HN—CH$_2$—CO—, wherein the terminal carbonyl carbon in the chemical formula (Gly) is bonded to the N atom in the chemical formula (G1), and wherein the terminal nitrogen atom in the chemical formula (Gly) is bonded to the carbonyl carbon in the chemical formula (G1), wherein GlyGly in the sequence shown by SEQ ID NO: 4, 6, 13 or 18 is an atomic group represented by the following chemical formula (G2), and when no base is bonded to the 5' terminus, a hydrogen atom (H) is bonded to the 5' terminus:

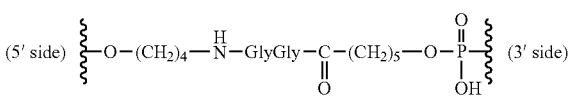

(G2)

wherein in the chemical formula (G2), GlyGly is an atomic group represented by the following chemical formula (GlyGly): —HN—CH$_2$—CO—HN—CH$_2$—CO—, wherein the terminal carbonyl carbon in the chemical formula (GlyGly) is bonded to the N atom in the chemical formula (G2), and wherein the terminal nitrogen atom in the chemical formula (GlyGly) is bonded to the carbonyl carbon in the chemical formula (G2), wherein TPA in the sequence shown by SEQ ID NO: 15, 16 or 17 is an atomic group represented by the following chemical formula (TPA), and when no base is bonded to the 5' terminus, a hydrogen atom (H) is bonded to the 5' terminus:

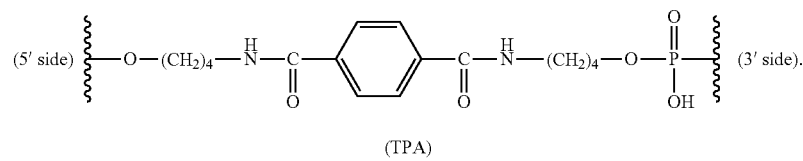

(TPA)

\* \* \* \* \*